United States Patent [19]
Arlinghaus et al.

[11] Patent Number: 6,107,457
[45] Date of Patent: Aug. 22, 2000

[54] BCR-ABL DIRECTED COMPOSITIONS AND USES FOR INHIBITING PHILADELPHIA CHROMOSOME STIMULATED CELL GROWTH

[75] Inventors: Ralph B. Arlinghaus; Jiaxin Liu, both of Bellaire; Dai Lu, Houston; Gabriel Lopez-Berestein, Bellaire, all of Tex.

[73] Assignee: Board of Regents, The University of Texas System, Austin, Tex.

[21] Appl. No.: 08/390,353

[22] Filed: Feb. 16, 1995

[51] Int. Cl.$^7$ ............................... C07K 7/00; C07K 14/00
[52] U.S. Cl. .......................... 530/300; 530/324; 530/326; 530/327; 530/328; 530/329; 530/330
[58] Field of Search ................................ 514/2; 530/300, 530/324, 326, 327, 328, 329, 330, 352

[56] References Cited

U.S. PATENT DOCUMENTS

| | | | |
|---|---|---|---|
| 4,599,305 | 7/1986 | Witte et al. | 435/7 |
| 5,334,761 | 8/1994 | Gebeyehu et al. | 564/197 |
| 5,763,571 | 6/1998 | Avruch et al. | 530/324 |
| 5,795,859 | 8/1998 | Rathjen et al. | 514/12 |

FOREIGN PATENT DOCUMENTS

| | | |
|---|---|---|
| 0 338 713 A1 | 10/1989 | European Pat. Off. . |
| WO 92/21032 | 11/1992 | WIPO . |

OTHER PUBLICATIONS

Lu et al., "Tyrosine Phosphorylation of P160 BCR by P210 BCR–ABL", *Blood*, 82(4):1257–1263, 1993.

Maxwell et al., "Analysis of P210$^{bcr-abl}$ Tyrosine Protein Kinase Activity in Various Subtypes of Philadelphia Chromosome–positive Cells from Chronic Myelogenous Leukemia Patients", *Cancer Research*, 47:1731–1739, 1987.

Druker et al., "Tyrosine Phosphorylatino of rasGAP and Associated Proteins in Chronic Myelogenous Leukemia Cell Lines," *Blood*, 79(9):2215–2220, 1992.

Hou et al., "An Interleukin–4–Induced Transcription Factor: IL–4 Stat," *Science*, 265:1701–1706, 1994.

Liu et al., "BCR–ABL tyrosine kinase is autophosphorylated or transphosphorylates P160 BCR on tyrosine predominantly within the first BCR exon," *Oncogene*, 8:101–109, 1993.

McWhirter et al., "A Coiled–Coil Oligomerization Domain of Bcr is Essential for the Transforming Function of Bcr–Abl Oncoproteins," *Molecular and Cellular Biology*, 13(12):7587–7595, 1993.

McWhirter and Wang, "An actin–binding function contributes to transformation by the Bcr–Abl oncoprotein of Philadelphia chromosome–positive human leukemias," *The EMBO Journal*, 12(4):1533–1546, 1993.

Okabe et al., "Effect of Herbimycin A, an Antagonist of Tyrosine Kinase, on bcr/abl Oncoprotein–Associated Cell Proliferations: Abrogative Effect on the Transformation of Murine Hematopoietic Cells by Transfectin of a Retroviral Vector Expressing Oncoprotein P210$^{bcr/abl}$ and Preferential Inhibition on Ph$^1$–Positive Leukemia Cell Growth," *Blood*, 80(5):1330–1338, 1992.

Pawson and Gish, "SH2 and SH3 Domains; From Structure to Function," *Cell*, 71:359–362, 1992.

Pendergast et al., "BCR–ABL–Induced Oncogenesis Is Mediated by Direct Interaction with the SH2 Domain of the GRB–2 Adaptor Protein," *Cell*, 75:175–185, 1993.

Puil et al., "Bcr–Abl oncoproteins bind directly to activators of the Ras signalling pathway," *The EMBO Journal*, 13(4):764–773, 1994.

Tauchi et al., "Coupling between p210bcr–abl and Shc and Grb2 Adaptor Proteins in Hematopoietic Cells Permits Growth Factor Receptor–indpendent Link to Ras Activation Pathway," *J. Exp. Med.*, 179:16–175, 1994.

Tauchi et al., "SH2–containing Phosphotyrosine Phosphatase Syp Is a Target of p210bcr–able Tyrosine Kinase," *The Journal of Biological Chemistry*, 269(21):15381–15387, 1994.

Hoeve et al., "Tyrosine Phosphorylation of CRKL in Ph–Positive Leukemia," *Blood*, 84(6):1731–1736, 1994.

Hoeve et al., "Cellular Interactions of CRKL, and SH2–SH3 Adaptor Protein," *Cancer Research*, 4:2563–2567, 1994.

*Primary Examiner*—John S. Brusca
*Assistant Examiner*—Sean McGarry
*Attorney, Agent, or Firm*—Arnold, White & Durkee

[57] ABSTRACT

Compositions comprising a mixture of peptides that bind to molecules involved in Bcr-Abl oncoprotein function are disclosed. In addition, expression of functional BCR protein (p160 BCR) or amino terminal fragments thereof (159, 221 and 413 amino terminal residues) by way of retrovirus vectors will oppose the biological function of Bcr-Abl (p160 BCR) or inactivate Bcr-Abl tyrosine kinase function or its signal transduction function. Bcr and Abl peptides, either tyrosine phosphorylated or unphosphorylated, that bind to a region near the amino terminus of Bcr to prevent formation of tetramer Bcr-Abl molecules, that bind to the SH2 domain of Grb2, to sites on tyrosine phosphorylated Shc protein, to sites of Crkl, and to an SH2 domain of Ras Gap comprise particular peptide preparations of the invention. The peptides and polypeptides inhibit Bcr-Abl oncoprotein activation, or block the oncogenic signal generated by the Bcr-Abl oncoprotein and, thereby, inhibit growth and induce cell death of leukemia cells expressing the oncoprotein. Methods for processing bone marrow using the peptide and polypeptide compositions of the invention are also provided. Stem cells present in bone marrow may thus be enriched for Philadelphia chromosome-negative cells prior to transplantation, particularly as part of autologous bone marrow transplant therapy of leukemia, including CML, ALL and AML.

21 Claims, 18 Drawing Sheets

Anti-BCR1-16

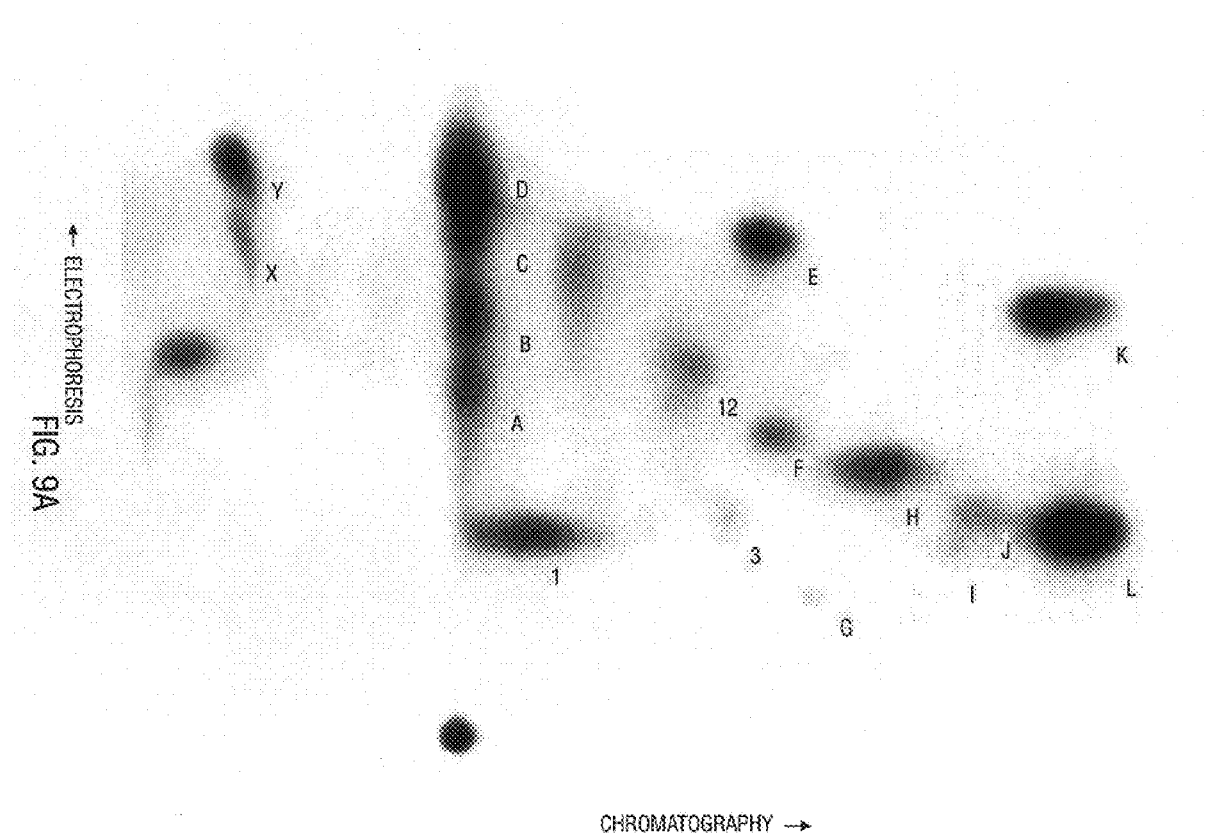

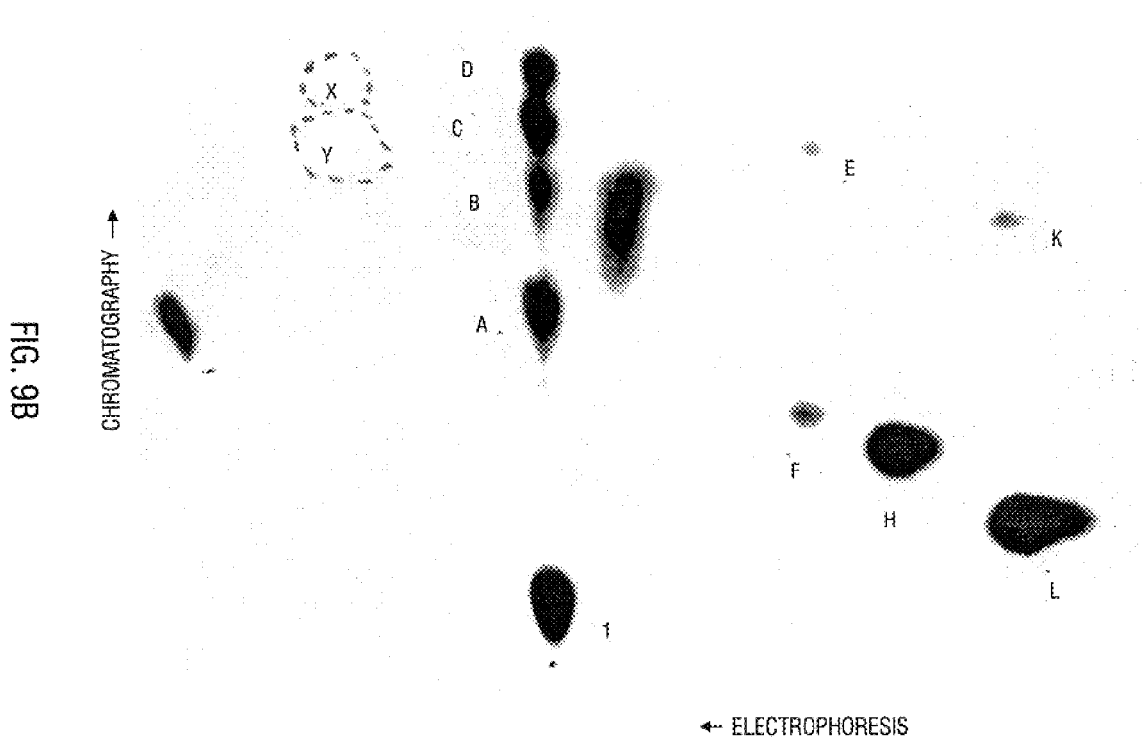

Anti-Grb2

IP: Anti-BCR

WB: Anti-Grb2

BCR-ABL DIRECTED COMPOSITIONS AND USES FOR INHIBITING PHILADELPHIA CHROMOSOME STIMULATED CELL GROWTH

FIELD OF THE INVENTION

The present invention relates generally to the field of malignant cell proliferation. More particularly, it concerns methods to limit Philadelphia chromosome-positive cell growth with peptide or protein molecules designed to inhibit various signal transduction pathways, in particular, the activation of the Ras protein; and thereby, enrich Philadelphia chromosome-negative cells in bone marrow culture. Methods for treating chronic myelogenous leukemia (CML), acute lymphocytic leukemia (ALL) and acute myelogenous leukemias (AML) pathologies are also provided.

BACKGROUND OF THE INVENTION

The Philadelphia chromosome (Ph[1]) is associated with the bulk of chronic myelogenous leukemia (CML) patients (more than 95%), 10–25% of acute lymphocytic leukemia (ALL) patients, and about 2–3% of acute myelogenous leukemias (AML). This abnormal chromosome fuses most of the ABL gene to the 5' two-thirds of the BCR gene. A number of different kinds of evidence support the contention that Bcr-Abl oncoproteins, such as p210 and p185 BCR-ABL, are causative factors in these leukemias[1]. The malignant activity is due in large part to the Bcr-Abl protein's highly activated protein tyrosine kinase activity and its abnormal interaction with protein substrates[1,2].

The Bcr-Abl oncoprotein p210 Bcr-Abl is associated with both CML and ALL, whereas the smaller oncoprotein, p185 BCR-ABL, is associated with ALL patients, although some CML patients also express p185[1]. Some reports suggest that Bcr-Abl oncoproteins, p210 and p185 BCR-ABL, function at least in part by activating the Ras pathway. The RAS gene is a proto-oncogene involved in controlling normal cell growth. When continuously activated, the Ras protein becomes a potent cancer gene product. Bcr-Abl oncoproteins have been observed by the present inventors and others to perturb normal Ras function[3].

The mechanism by which Bcr-Abl oncoproteins activate p21 Ras involves several factors. One event involves the autophosphorylation of the Bcr-Abl oncoprotein on tyrosine residues within the coding sequence of the first Bcr exon[4]. This finding was unexpected, as it had previously been postulated that Bcr-Abl phosphorylates itself on Abl tyrosines, not Bcr tyrosine residues. Several adaptor proteins have been implicated in Ras-activation as well. FIG. 2 lists several such adaptor proteins that contain SH2/SH3 motifs. Such domains have been observed in proteins involved in transmitting growth signals to the nucleus[5].

Grb2 is an adaptor protein that binds to tyrosine phosphorylated receptor proteins. Bcr-Abl induced oncogenesis has also been reported to be mediated by direct interaction with the SH2 domain of the Grb2[3,16]. Grb2 also binds mSos1, a GTP exchange factor (see FIG. 3). The latter activates Ras by forming GTP/Ras. GTP/Ras in turn activates Raf, a serine/threonine protein kinase that activates Mek. Mek is a kinase that phosphorylates and activates MAP kinase. The latter is believed to activate and/or regulate various transcription factors (i.e. c-Jun), resulting in cell growth (FIG. 4).

Another protein/protein interaction that has been examined in relation to Bcr-Abl induced malignancy concerns the formation of tetramer structures. In Philadelphia chromosome-positive human leukemias, the c-abl proto-oncogene on chromosome 9 becomes fused to the bcr gene on chromosome 22, and chimeric Bcr-Abl proteins are produced. The fused Bcr sequences activate the tyrosine kinase, actin-binding, and transforming functions of Abl. Activation of the Abl transforming function has been shown to require two distinct domains of Bcr: domain 1 (Bcr amino acids 1 to 63) and domain 2 (Bcr amino acids 176–242)[6] Domain 1 of Bcr has been shown to form a homotetramer[6] (FIG. 7A and FIG. 7B). Disruption of the coiled coil by insertional mutagenesis inactivates the oligomerization function and the ability of Bcr-Abl to transform Rat-1 fibroblasts. The Bcr-Abl tetramer activates its inherent Abl tyrosine kinase activity, its actin binding function, and its cellular transformation function[6].

Another peptide that has been implicated in the malignant effects of Bcr-Abl involves Shc[16]. Crkl is another adaptor molecule that forms a protein/protein interaction with Bcr-Abl[8,9,17]. Still another adaptor molecule that interacts with Bcr-Abl is p120 Ras Gap[7].

Despite the description of events/molecules involved in Bcr/Abl function and pathologies associated with the activities of its gene product therewith, comprehensive strategies for controlling the activation of the Ras oncogene have not been developed. Thus, a need continues to exist in the medical arts for clinical approaches that target effectively and specifically inhibit Ras activation. Such novel techniques would also provide alternatives in inhibiting Philadelphia chromosome-positive cells in tissues, such as in bone marrow.

It is an object of the present invention to define specific peptide sequences from Bcr-Abl that inhibit Bcr-Abl activation of Ras function. Such peptides identify important binding sites on Bcr-Abl for adaptor molecules such as Grb2. A further object of the invention is to identify peptides or a single polypeptide that include important binding sites for other principal targets of Bcr-Abl oncoproteins together with Grb2-directed peptides. A further object of the invention is to provide Bcr as a negative regulator of Bcr-Abl function. Another object of the invention is to provide methods for processing bone marrow, and particularly for enriching Philadelphia chromosome-negative cells in bone marrow culture. Another object of the invention is to provide liposome associated preparations of peptides that mimic binding sites of the principal targets of Bcr-Abl oncoproteins.

SUMMARY OF THE INVENTION

The present invention solves one or more limitations of the prior art by providing for the first time compositions for inhibiting and/or limiting the effects of Bcr/Abl, in particular, the effects on Ras activation. According to the present invention, the number of cells that are Philadelphia chromosome-positive may be reduced through the use of particularly identified peptides. More specifically, the present inventors identified various peptides and protein compositions of the invention, which should interfere with the growth and proliferation of Bcr-Abl expressing human leukemic cells by interfering with activation of Ras or other important molecules in growth signal transduction pathways. In some embodiments, the compositions include a peptide or peptides having a segment of a Bcr-Abl amino acid sequence that includes a combination of several tyrosine residues found important by the present inventors in Bcr-Abl induction. These include tyrosines 177, 283 and 360. While it is envisioned that various combinations of peptide or peptides that include at least two of the tyrosine regions will be useful in the described compositions and methods, a composition that includes peptides including regions related to all three of these tyrosine residues are envisioned as preferred in some applications.

The expression of various combinations of peptides including the ones described above will in some embodiments be prepared that bind several signal transduction molecules (Grb2/mSos1, Shc, Ras Gap, Crkl) thereby preventing these molecules from carrying out their growth-promoting functions. In these embodiments, the composition may be further defined as comprising a peptide selected from the group consisting of: a peptide that binds an ABl SH3 binding site on Crkl, a peptide that binds an Abl SH3 binding protein-rich region of Shc, a peptide that binds an SH2 domain of p120 Ras Gap, and a peptide or protein that binds an N-terminal coiled-coil region of Bcr. Ultimately, a more complete inactivation of signal transduction pathways, in this case, primarily the Ras pathway, may be achieved.

The present inventors observed that the Bcr protein contains the consensus binding site Y*VNV (residues 177–180, SEQ ID NO:13) for Grb2. Through the interaction of this consensus binding site of Bcr, the Ecr-Abl oncoprotein forms a complex with Grb2. Tyrosine phosphorylation of Bcr sequences at tyrosine 177 has been observed by the present inventors to cause Grb2/mSos1 to bind membrane-bound Bcr-Abl. This is proposed by the present inventors to activate p21 Ras (FIG. 5). By using peptides that have these defined binding sequences, interference with Grb2 binding to Bcr-Abl will block Bcr-Abl induced malignant effects particularly when used in combination with one or more of the Shc, Crkl, SH2 or p120 Ras Gap binding sequences disclosed.

In some embodiments, the compositions also include peptides that have a sequence corresponding to the first 63–71 (i.e., 1–63 or 1–71) amino acids of Bcr, this sequence including a possible phosphorylated tyrosine residue at amino acid 70. Expression of this peptide or peptides that include at least a sequence corresponding to Bcr 28–68, in leukemic cells will interfere with the malignant activities of Bcr-Abl oncoproteins by blocking its tyrosine kinase activity. In doing same, a method for inhibiting Bcr-Abl induced malignancy is provided.

The inventors' studies have demonstrated that Bcr peptide GHGQPGADAEKPFp.YI$_{177}$VNVE, SEQ ID NO:8 (residues 164–181) strongly binds to the SH2 binding site on Grb2[16]. These peptides are included in some embodiments of the claimed compositions of the invention together with others described herein. Other tyrosine binding sites outside of the 164–181 Bcr region identified include a region 353–364 BCR (tyrosine at 360), region 255–293 Bcr (tyrosine 283) and other tyrosines at 70, 231, 246 and 279. Based on these findings, peptides that include at least a 4-mer or 5-mer sequence that includes the tyrosine of importance are expected to provide effective molecules in the compositions for Bcr-Abl inhibition. For example, a sequence that includes at least Bcr 176–180, such as a 12-mer corresponding to sequence Bcr 168–180, together with sequence that includes an about 5- to 7-mer region surrounding tyrosine 279, such as Bcr 279–285, and a 5- to 7-mer region surrounding tyrosine 360, such as Bcr 359–363, constitute peptides that would be expected to provide the Bcr-Abl inhibitory activity described herein.

As noted above, the compositions of the invention may in some embodiments further comprise a peptide that binds an Abl SH3 binding protein-rich region of Shc. The Shc-binding peptides form a complex with Bcr-Abl and is tyrosine phosphorylated by Bcr-Abl. Shc also binds to Grb2. This complex also has potential to activate Ras. Although the SH2 domain of Shc might be involved, it is proposed by the present inventors that the SH2 domain of Abl binds to a proline-rich sequence within Shc. This peptide is further defined as having a sequence corresponding to Bcr 299–351, or mimetics thereof.

A further protein/protein interaction of the present compositions involves Crkl and Bcr-Abl. Crkl has a structure similar to Crk (the oncogene of V-Crk) (FIG. 2)[8,9]. Crk is an SH2/SH3-containing adaptor protein first discovered in an avian sarcoma virus[8]. Crkl is tyrosine phosphorylated in cell lines expressing Bcr-Abl and in uncultured blood cells from patients that express the Bcr-Abl oncoprotein[17]. The Crkl protein product is a 38-kDa protein that is expressed in several cell types. This p38 is phosphorylated on tyrosine by Abl and Bcr/Abl and forms complexes in vivo with both Abl and Bcr/Abl. In addition, Crkl is capable of binding to mSos1[9]. Peptides that mimic the Abl SH3 binding site on CRKL are also components of some embodiments of the present invention.

Another Bcr/Abl peptide included in some embodiments of the invention is characterized by its interaction with p120 Ras Gap. This peptide likely involves tyrosine 279 and a tyrosine outside of the first exon of Bcr. As defined above, peptides of this nature are described more particularly as peptide that binds an SH2 domain of p120 Ras Gap.

In an even further embodiments, the composition may comprise a peptide or protein that binds an N-terminal coiled-coil region of Bcr and may have a sequence corresponding to positions 28–68 of Bcr, such as 1–159, 1–221 or 1–413 of Bcr. The peptide or protein that binds an N-terminal coiled-coil region of Bcr is further defined as having a sequence corresponding to positions 1–71 or 1–63 of Bcr.

According to some embodiments of the invention, inhibition of Philadelphia chromosome-positive cells is achieved by treating cells that include Philadelphia positive cells to a composition that includes any of the combination of peptides described above. Such may be achieved, by example, through expression of the first 63–71 amino acids of Bcr (or fragments that include residues 28–68), Bcr peptide 164–181 (housing tyrosine 177), Bcr peptide 255–293 (that houses tyrosine 283), and Bcr peptide 353–364 (housing tyrosine 360) in the mixture of cells. In other embodiments, the composition includes a peptide having a sequence that binds at least Bcr tyrosine residues 177, 283 or 360, or all of these Bcr tyrosine sites, together with a peptide selected from the group consisting of a peptide that binds an SH2 binding site on Grb2, a peptide that binds an Abl binding site on Crkl, a peptide that binds an SH2 domain of p120 Ras Gap, and a peptide that binds an N-terminal coiled-coil region of Bcr. Sequences that include the herein disclosed peptides are provided in SEQ ID NO:1–12. The compositions of the present invention may also in some embodiments include a pharmaceutically acceptable carrier, such as Ringers solution, saline, and the like.

The present invention also comprises a retrovirus that contains a sequence or sequences encoding at least one of the described Bcr tyrosine peptides, such as 164–181 Bcr, alone or together with a peptide selected from the group consisting of: a Bcr-Abl peptide that binds the Abl binding site on CRKL, a Bcr-Abl peptide that binds an Abl SH3 binding proline-rich region of SHC and a peptide that binds an SH2 domain of p120 Ras Gap. An amphotropic retrovirus, defective in replication but capable of infecting bone marrow cells from patients, would be constructed that would express the above-named peptides either singly or as part of a fused polypeptide. Alternatively, individual retroviruses expressing the first 71 amino acids of Bcr fused separately to the peptides in question would be constructed. The methods of the invention comprise introducing sequences individually, as a mixture, or as a single polypeptide into bone marrow containing Philadelphia chromosome-positive cells from CML/ALL patients prior to reimplanting for an autologous bone marrow transplant. This treatment would block the leukemic effects of Bcr-Abl in those leukemic cells that are present in the stem cell population.

Another embodiment of the invention comprises compositions of one or more of the above described peptides or peptides containing them, or fragments of them, in association with liposomes. In this aspect of the invention, the peptides would be encapsulated into liposomes. These compositions may then be used directly in patients as a drug, or for use in processing/treating stem cells (ex vivo), particularly stem cells from patients undergoing a bone marrow transplant. Bone marrow samples treated in this manner could then be used, for example, to enhance the immunocompetency of the transplant recipient.

In particular preparations, the compositions may further include a pharmaceutically acceptable carrier, such as a Ringers solution, saline, or like carrier as known to those of ordinary skill in the pharmaceutical arts.

The approaches of the present invention provide an improvement over current strategies (i.e., anti-sense Bcr-Abl approaches) in that the activity of Bcr-Abl would be inhibited while at the same time neutralizing more than one of the principal targets of Bcr-Abl oncoproteins.

As described in the above compositions, the Bcr-Abl amino acid sequence that includes tyrosine 177 in some embodiments has the sequence of SEQ ID NO:8, or fragment thereof and is further defined as binding an SH2 binding site on Grb2. This composition may further comprise a peptide that binds an Abl binding site on Crkl, or a peptide that bind s an Abl SH3 binding proline-rich region of Shc, or a peptide that binds an SH2 domain of p120 Ras Gap, or any mixture thereof. The Bcr-Abl peptides of the present invention may also inhibit other adapter proteins in addition to those cited herein as being in the Ras activation pathway. Functionally equivalent peptides as described herein are also contemplated by the present inventors.

In some embodiments, the peptide or peptides having a Bcr-Abl amino acid sequence that includes tyrosine 177, 283, and 360 has a sequence corresponding to position 164–181 (SEQ ID:8), 255–293 (SEQ ID:11), and 353–364 (SEQ ID:10) of Bcr, respectively.

The Bcr-Abl peptide or peptides of particular preparations of the composition may be further defined as having a sequence as in SEQ ID NO:1—SEQ ID No:12 or fragments thereof that include at least the defined regions described herein (see Table A).

In some embodiments of the present invention, the Bcr-Abl peptide or peptides may be in the form of a polypeptide, or may be associated with a liposome, or both. The composition may also comprise a pharmaceutically acceptable carrier.

A vector including a sequence encoding the Bcr-Abl peptide, peptides, or protein of the present invention is also contemplated as part of the present invention. The vector may be a plasmid, a retrovirus, an adenovirus or an expression vector as described herein. A preferred retrovirus comprises a sequence or SEQ ID NO:1–12, or fragments thereof; and a more preferred sequence is that of SEQ ID NO:5, or fragments thereof.

One embodiment of the expression vector includes a sequence encoding the normal Bcr protein. The normal Bcr protein has 1271 amino acids and the sequence is presented in M. L. Campbell and R. B. Arlinghaus, "Current Status of Bcr Gene Involvement with Human Leukemia", Advances in Cancer Research, 57:227–255, 1991, which is incorporated by reference herein.

A method for enriching Philadelphia chromosome-negative cells in a mixture of cells containing Philadelphia chromosome-positive cells is a further aspect of the present invention. The method comprises the steps of adding the composition of Bcr-Abl peptides of the present invention to the mixture of cells to provide a culture enriched for Philadelphia chromosome-negative cells. In one embodiment, the cells comprise bone marrow cells. In this method, Philadelphia chromosome-negative cells are enriched relative to numbers naturally occurring in a bone marrow sample containing Philadelphia chromosome positive cells. The composition of Bcr-Abl peptides is further defined as comprising a peptide having a sequence as defined in SEQ ID NO:1–12 or a polypeptide of any of the said peptides. The peptides may be delivered to the cells by way of a retroviral delivery system as defined herein, or by way of liposomal delivery.

A method of treating bone marrow having Philadelphia chromosome-positive cells to prepare bone marrow enriched for Philadelphia chromosome-negative cells for bone marrow transplant is another embodiment of the invention. In one embodiment, the method comprises the step of adding a vector including a sequence encoding a Bcr peptide having a Bcr-Abl amino acid sequence that includes tyrosine 177, 283, and 360. The composition may further comprise a peptide selected from the group consisting of a peptide that binds an N-terminal coiled-coil region of Bcr and a sequence encoding a peptide that binds an SH2 binding site on Grb2, a peptide that binds an Abl binding site on Crkl, and a peptide that binds an SH2 domain of p120 Ras Gap, to the bone marrow. The peptide encoded by the retroviral vector is further defined as having a sequence corresponding to SEQ ID NO:1—SEQ ID NO:12. In this method, Philadelphia chromosome-negative cells are enriched relative to numbers naturally occurring in a bone marrow sample containing Philadelphia chromosome-positive cells. By way of example, either a retroviral vector or adenovirus may be used in various of the described methods.

A method for treating leukemia in an animal is a further aspect of the present invention, comprising the steps of treating a tissue sample containing Philadelphia chromosome-positive cells from the animal with a therapeutically effective amount of any of the Bcr-Abl composition of the present invention; and introducing said treated tissue to the animal, wherein Philadelphia chromosome-negative cells are enriched relative to numbers naturally occurring in the tissue containing Philadelphia chromosome-positive cells. A preferred tissue is bone marrow and the composition is further defined as comprising a peptide having a sequence as defined in SEQ ID NO:8, SEQ ID NO:10 or SEQ ID NO:11.

Modifications and changes may be made in the sequence of the peptides of the present invention except for the tyrosine residue that is the site of phosphorylation and the asparagine residue at position 179 of SEQ ID NO:1 and still obtain a peptide having like or otherwise desirable characteristics. For example, certain amino acids may be substituted for other amino acids in a peptide without appreciable loss of interactive binding capacity. Since it is the interactive capacity and nature of an amino acid sequence that defines the peptide's functional activity, certain amino acid sequences may be chosen (or, of course, its underlying DNA coding sequence) and nevertheless obtain a peptide with like properties. It is thus contemplated by the inventor that certain changes may be made in the sequence of a peptide (or underlying DNA) without appreciable loss of its ability to function.

Substitution of like amino acids can be made on the basis of hydrophilicity. U.S. Pat. No. 4,554,101, incorporated herein by reference, states that the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent peptide. In such changes, the substitution of amino acids whose hydrophilicity values are within ±2 is preferred, those which are within ±1 are particularly preferred, and those within ±0.5 are even more particularly preferred.

One of skill in this art in light of the present disclosure would realize that the tyrosine site of phosphorylation of the peptides is not amenable to replacement, nor is the asparagine at position 179 of SEQ ID NO:1. Functional equivalents of other amino acids are acceptable in the present invention.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Two designations for amino acids are used interchangeably throughout this application, as is common practice in the art. Alanine=Ala (A); Arginine=Arg (R); Aspartate=Asp (D); Asparagine=Asn (N); Cysteine=Cys (C); Glutamate= Glu (E); Glutamine=Gln (Q); Glycine=Gly (G); Histidine= His (H); Isoleucine=Ile (I); Leucine=Leu (L); Lysine=Lys (K); Methionine=Met (M); Phenylalanine=Phe (F); Proline= Pro (P); Serine=Ser (S); Threonine=Thr (T); Tryptophan= Trp (W); Tyrosine=Tyr (Y); Valine=Val (V).

While discussion has focused on functionally equivalent polypeptides arising from amino acid changes, it will be appreciated that these changes may be effected by alteration of the encoding DNA, taking into consideration also that the genetic code is degenerate and that two or more codons may code for the same amino acid.

The synthesis of peptides is readily achieved using conventional peptide synthetic techniques such as the solid phase method (e.g., through the use of commercially available peptide synthesizer such as an Applied Biosystems Model 430A Peptide Synthesizer, Foster City, Calif., or Vega Synthesizer, DuPont Inc., Wilmington, Del.). It is desirable for the amino terminal end of synthetic peptides to be protected from degradation by having an N-terminal acetyl group. This can be accomplished during synthesis of the peptide by using acetic anhydride to acetylate the N-terminal end. Similarly, protection for the carboxyl end may be achieved by forming an amide bond as described in Example 2. These protecting groups will prevent the synthetic peptides from being degraded by proteolytic enzymes once they are introduced into a cell. Peptides synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in sterile aqueous solutions for fairly long periods of time if desired, e.g., up to six months or more, in virtually any aqueous solution without appreciable degradation or loss of immunogenic activity. However, where extended aqueous storage is contemplated, it will generally be desirable to include agents including buffers such as Tris-HCl or phosphate buffers to maintain a pH of 7.0 to 7.5. Moreover, it may be desirable to include agents which will inhibit microbial growth, such as sodium azide or merthiolate. For extended storage in an aqueous state, it will be desirable to store the solutions at 4° C., or more preferably, frozen. Of course, where the peptide(s) are stored in a lyophilized or powdered state, they may be stored virtually indefinitely, e.g., in metered aliquots that may be rehydrated with a predetermined amount of water (preferably distilled) or buffer prior to use.

The present invention provides a most practical system for purging human bone marrow samples of leukemic patients. In the typical clinical management of a patient with leukemia, the patient is given chemotherapy (for example, Daunomycin, Ara-C, GMCSF). The chemotherapy treatment will then typically generate cytogenetic remissions in 50% of the treated patients. Cytogenetic remission is defined as a reduction in the ratio of leukemia cells (Philadelphia chromosome-positive) to normal cells (Philadelphia chromosome-negative) from about 10,000/1 to 1/1. The bone marrow of these patients is then subjected to separations based on the immunophenotype of the patient. The inventors seek to define a DR negative lineage CD33 negative, DC34 positive phenotype (i.e., through fractionation of a DR negative CD34 cell line). This separation, based on immunophenotype, will, in most cases, reduce the ratio of leukemic to normal cells by another 2 logs (100×). By then employing the described BCR-peptide treatment methods to bone marrow samples of the patient described herein, the ratio of leukemia cells (Philadelphia chromosome-positive) to normal cells may advantageously be expected to be reduced by still another 2 logs, and sometimes 3 logs.

Generally stated, the present invention provides a method of treating leukemia in a patient comprising: preparing an essentially leukemia cell-free autologous bone marrow sample by treating the bone marrow sample with peptides that bind an Shc binding site on Grb2, a sequence that binds an SH2 domain of p120 Ras Gap, and a sequence that binds a tyrosine residue of an N-terminal region of Bcr corresponding to position 177, 283 or 360; and administering the treated bone marrow sample to the patient. Alternatively, the sample may be treated with a peptide having a sequence that binds Bcr tyrosine residues at positions 177, 283 and 360. In some embodiments, these sequences are part of a retroviral vector that is used to treat the tissue.

For the purpose of this invention, an autologous bone marrow sample is defined as a sample of bone marrow intended to comprise the donor's own bone marrow transplant treatment.

More particularly, the present invention provides a method for treating leukemia in a patient comprising the following steps: (1) preparing BCR peptides having a composition comprising a Bcr-Abl peptide or peptides capable of inhibiting Bcr-Abl induced activation of Ras, said peptide or peptides having a Bcr-Abl amino acid sequence that includes tyrosine 177, 283, and 360 capable of selectively inducing cytotoxicity of leukemia cells (thereby providing an essentially leukemia cell-free autologous bone marrow sample); (2) obtaining a bone marrow sample from the patient with leukemia; (3) treating the bone marrow sample to a leukemia cell-cytotoxic amount of the BCR peptides, said amount being effective to inhibit and/or kill said leukemic cells, for a period of time sufficient to provide an essentially leukemia cell-free bone marrow sample; and (4) administering the essentially leukemia cell-free bone marrow sample to the patient to provide a treatment for leukemia in the patient. The ratio of leukemic cells to normal bone marrow cells in the patient will effectively be reduced through introduction of the treated bone marrow cells. At least a 2-log (100 fold) reduction in the ratio of leukemia cells to normal bone cells is expected through this method, and will therefore potentially provide a highly selective method of treating leukemia in the patient without damaging or inhibiting normal cells of the patient or treated patient bone marrow sample.

The present invention also provides methods for culturing bone marrow, and particularly methods for enriching Philadelphia chromosome-negative cells in culture. In one embodiment, the method comprises adding a composition comprising a peptide or peptides capable of inhibiting Bcr-Abl activation of Ras, said peptides having Bcr-Abl amino acid sequence that include tyrosine 177, 283 and 360, to a mixture of cells that include Philadelphia chromosome-positive cells to provide a culture enriched for Philadelphia chromosome-negative cells. This particular composition may, in other embodiments, include any one or all of the peptides selected from the group consisting of a peptide that binds an Abl binding site on CRKL, a peptide that binds an Abl SH3 binding proline-rich region of Shc or a peptide that binds an SH2 domain of p120 Ras Gap. Specific sequences that represent the above peptides are defined in SEQ ID NO:1–12. The peptides may be further defined as a polypeptide for particular applications. In some embodiments, the cells comprise bone marrow cells.

In one particular embodiment of the above described method, the composition added to the cells may include a retrovirus that include a sequence encoding the selected peptide or peptides defined herein. In other embodiments, the peptide or peptides, are associated with liposomes, and are in this form added to cells that include Philadelphia chromosome-positive cells.

As used in the description of the present invention, a composition of cells, such as bone marrow, is enriched for Philadelphia chromosome-negative cells where the number of Philadelphia chromosome-negative cells is increased relative to the numbers naturally occurring in a tissue containing Philadelphia chromosome-positive cells. Another object of the invention is to provide liposome associated preparations of peptides that mimic binding sites of the principal targets of Bcr-Abl oncoproteins, as well as in association with peptides that mimic Bcr and Abl sequences that bind the adapter molecules, such as Grb2.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A depicts a normal progenitor cell. FIG. 1B depicts a leukemic progenitor cell.

FIG. 6A shows a Western blot with Anti-Tyr antibody. Bcr-Abl induces tyrosine phosphorylation of Bcr221 and Bcr413 but not Bcr159, indicating that the first two tyrosines of Bcr are not targets for Bcr-Abl. The next tyrosine is at residue 177, and it is expected to be phosphorylated by Bcr-Abl[16]. Bcr221 is tyrosine phosphorylated, but as with Bcr413, only in the presence of Bcr-Abl. FIG. 6B shows a Western Blot of the same extracts probed with anti-Bcr 1–16. Note that all three Bcr proteins fragments are specifically expressed under both conditions.

FIG. 8A—p210-wild type; FIG. 8B—p210-F283; FIG. 8C—p210-F276; FIG. 8D—p185-F360.

FIG. 9A and FIG. 9B (Scanned images) show trypsin/V8 mapping of F283 and wild type p210 Bcr-Abl. The F283 mutant of p210 Bcr-Abl (FIG. 9B) expressed in COS-1 cells was compared to the map of p210 Bcr-Abl from K562 cells (FIG. 9A). In vitro labeling and mapping was performed. The dashed circles or Xs identify peptides lacking in the mutant.

DETAILED DESCRIPTION OF THE PREFERRED EMBODIMENTS

Figure 1A:
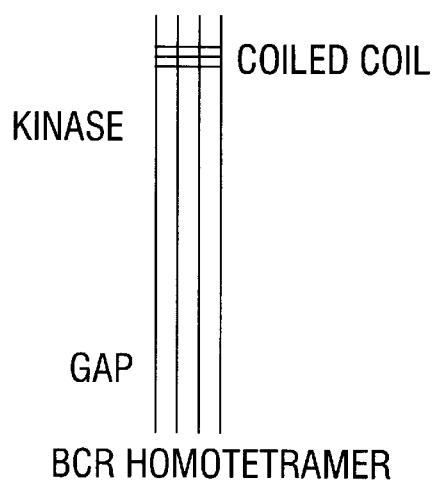
FIG. 1A and FIG. 1B provide models for Bcr and Bcr-Abl interaction.
Figure 1B:
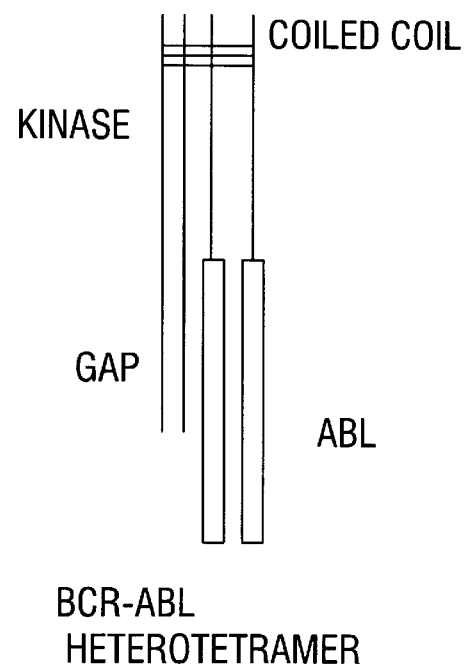
Figure 2:
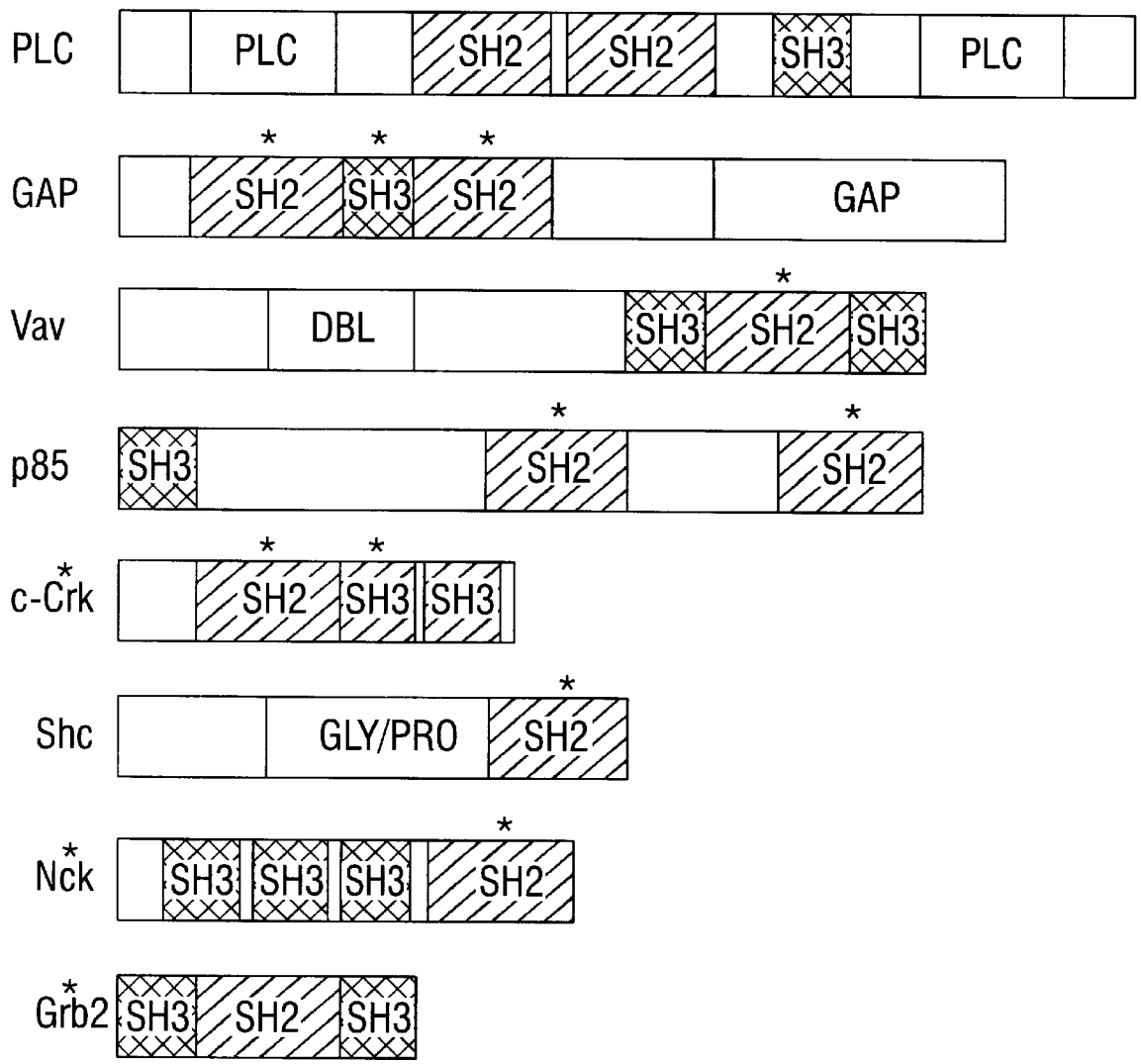
FIG. 2 provides a diagram of SH2/SH3 containing proteins involved in signal transduction.
Figure 3:
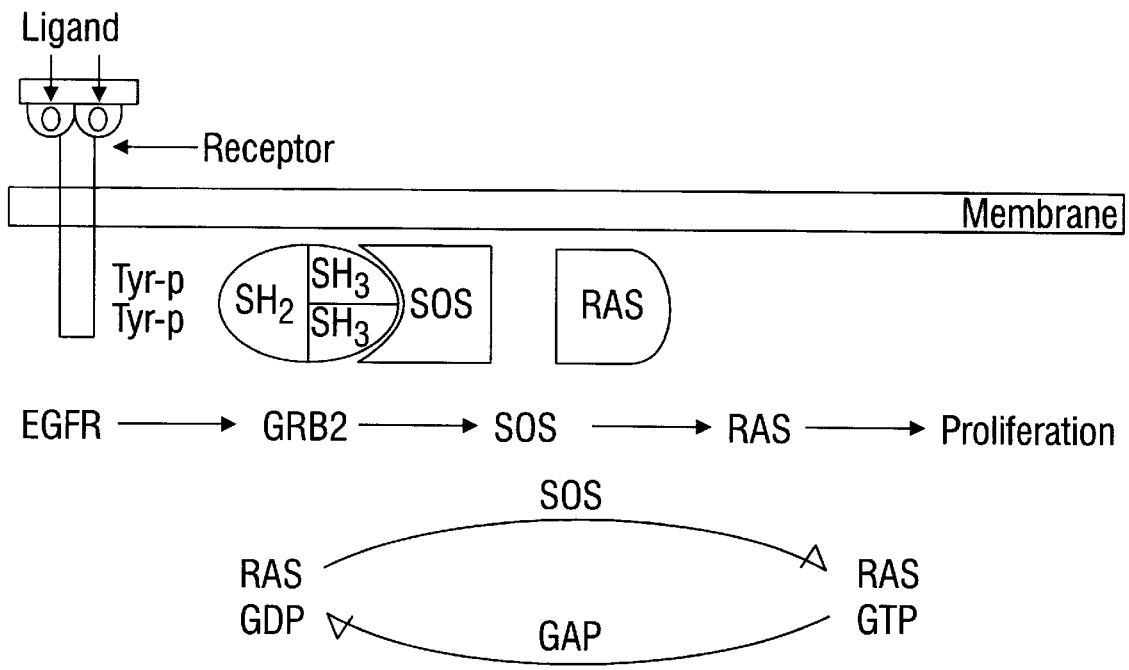
FIG. 3 outlines the activation of RAS by ligand receptor interaction.
Figure 4:
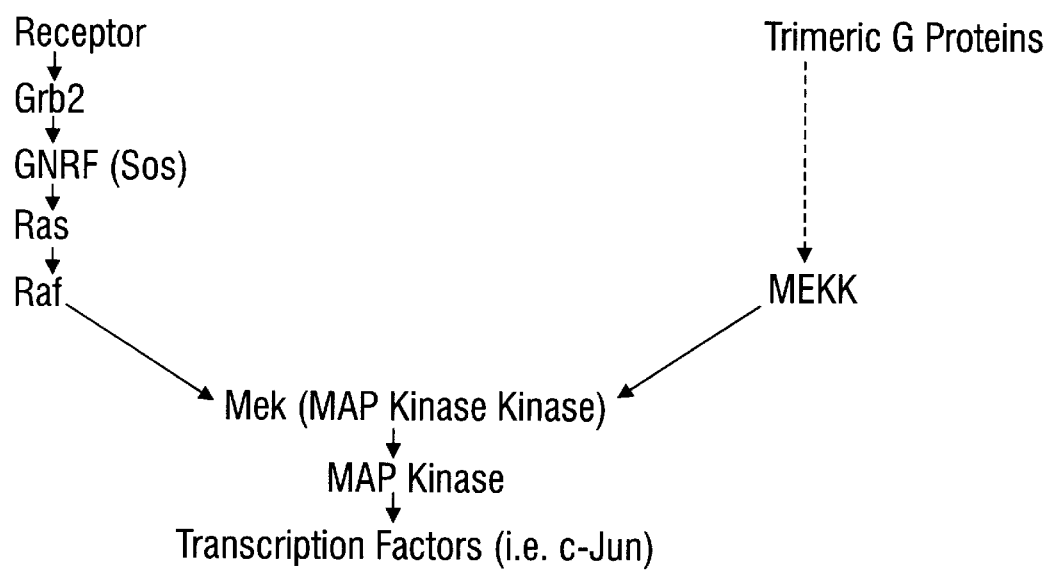
FIG. 4 outlines the pathway of activation of transcription factors by receptor/ligand interaction.
Figure 5:
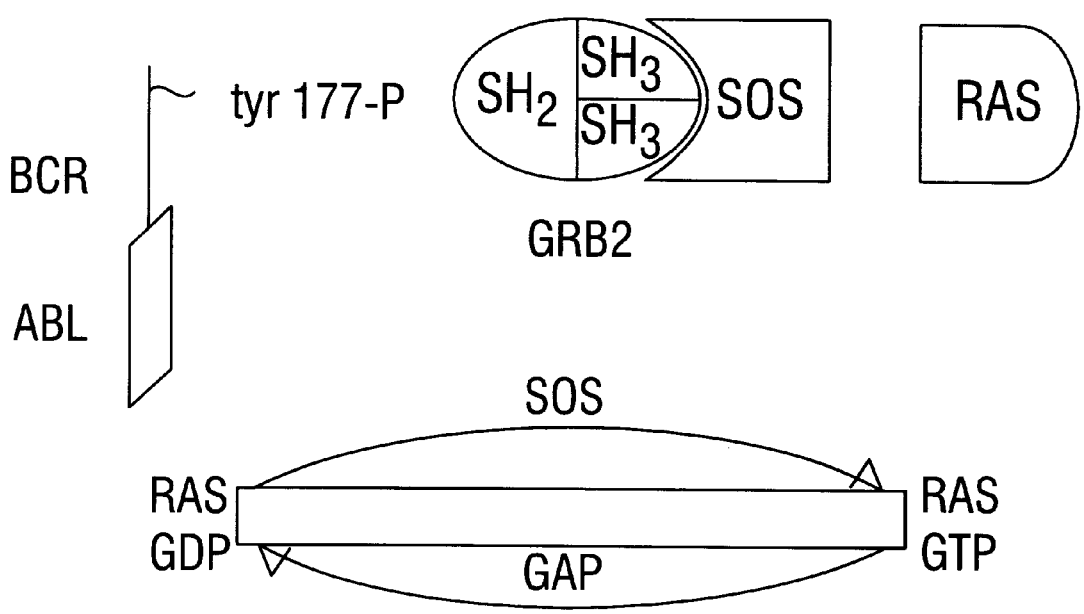
FIG. 5 outlines an activation pathway of Ras by Bcr-Abl.

The present invention provides a combination of peptides having BCR sequences including $Y^{177}$, $Y^{283}$ and $Y^{360}$ for the inhibition of BCR-Abl-adaptor protein interactions. This inhibition prevents the adaptor proteins from participating in the cascade that leads to Ras oncogene activation. The peptides may be phosphorylated at tyrosine residues or they may be provided in nonphosphorylated form because the target cell has the capacity to phosphorylate the peptides. The form of the peptide that binds to an adaptor protein is the phosphorylated form.

The Bcr-Abl peptides of the present invention may have 3–4 amino acids or may be 5, 6, 7, 8, 9, 10, 11, 12, 13, 14, 15, 16, 17, 18, 19 or 20 amino acids long. Longer peptides are also contemplated. The peptides have a tyrosine within their sequence at about the middle of the peptide. Peptides less than about 45 amino acids are synthesized chemically for providing to Philadelphia chromosome-positive cells whereas longer peptides are preferably provided by a plasmid or viral expression system. The administration of peptides to Philadelphia chromosome-positive cells is contemplated to be a repetitive or continuous supply of peptides.

The phosphorylated form of peptides is obtained in vitro by using standard methods for synthesis of peptides. The amino acid to be phosphorylated is introduced without side-chain protection. The terminal residue should be Boc protected by either direct incorporation of a Boc protected amino acid or acylation of the free amino group with $Boc_2O$. The resin is washed and placed into the reaction vessel. The peptidyl resin and reaction vessel are dried overnight under high vacuum at 40° C., sealed with a rubber septum and flushed with dry argon. An ampoule of DNA grade tetrazole is dissolved in dry DMF, DMA or $CH_3CN$ and 50 eq. are transferred to the reaction vessel using a dried argon flushed gas tight syringe. 10 eq. of di-t-butyl-N,N,-disopropylphosphoramidite are added to the reaction vessel again using a dried, argon flushed gas tight syringe, and gently agitated for 1 hour. The contents of reaction vessel are transferred to a sintered glass funnel and the resin washed with a generous volume of solvent. 20 eq. of t-butyl peroxide in DMF are added to the resin and left to stand for 30 mins. The resin is washed and dried in a normal manner. Standard methods are used for cleavage.

Biologically Functional Equivalent Amino Acids

It is believed that, where desired, modification and changes may be made in the structure of the polypeptides described herein and one may still obtain a molecule having like or otherwise desirable characteristics. Such changes may occur in natural isolates or may be synthetically introduced using site-specific mutagenesis as described below.

For example, certain amino acids may be substituted for other amino acids in a peptide without appreciable loss of interactive binding capacity such as peptides with sequence representing antigen-binding regions of antibodies (or, e.g., binding sites on substrate molecules). Since it is the interactive capacity and nature of a protein that defines that protein's biological functional activity, certain amino acid sequence substitutions can be made in a protein sequence (or, of course, its underlying DNA coding sequence) and countervailing properties (e.g., antagonistic v. agonistic). It is thus contemplated by the inventors that various changes may be made in the sequence of the peptides (or underlying DNA) without appreciable loss of their biological utility or activity.

The importance of the hydropathic index of amino acids in conferring interactive biologic function on a protein has been discussed generally by Kyte et al. (1982), or U.S. Pat. No. 4,554,101 to Hopp, both incorporated herein, wherein it is found that certain amino acids may be substituted for other amino acids having a similar hydropathic index or score and still retain a similar biological activity. As displayed in the table below, amino acids are assigned a hydropathic index on the basis of their hydrophobicity and charge characteristics. It is believed that the relative hydropathic character of the amino acid determines the secondary structure of the resultant protein, which in turn defines the interaction of the protein with substrate molecules.

TABLE 1

| AMINO ACID | HYDROPATHIC INDEX |
|---|---|
| Isoleucine | 4.5 |
| Valine | 4.2 |
| Leucine | 3.8 |
| Phenylalanine | 2.8 |
| Cysteine/cystine | 2.5 |
| Methionine | 1.9 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Aspartic Acid | −3.5 |
| Asparagine | −3.5 |
| Lysine | −3.9 |
| Arginine | −4.5 |

It is proposed that where an amino acid has a hydropathic index of within ±2 that of the base amino acid, and more preferably within ±1, such a change should nevertheless provide a protein having a similar, and perhaps even improved, functional activity. Thus, for example, it is proposed that isoleucine, which has a hydropathic index of +4.5, can be substituted for valine (+4.2) or leucine (+3.8), and one may still obtain a protein having similar biologic activity. Alternatively, at the other end of the scale, it is proposed that lysine (−3.9) can be substituted for arginine (−4.5), and so on.

Accordingly, these amino acid substitutions are generally based on the relative similarity of R-group substituents, for example, in terms of size, electrophilic character, charge, and the like. In general, exemplary substitutions which take various of the foregoing characteristics into consideration include the following:

TABLE 2

| ORIGINAL RESIDUE | EXEMPLARY SUBSTITUTIONS |
|---|---|
| Ala | Gly; Ser |
| Arg | Lys |
| Asn | Gln; His |
| Asp | Glu |
| Cys | Ser |
| Gln | Asn |
| Glu | Asp |

TABLE 2-continued

| ORIGINAL RESIDUE | EXEMPLARY SUBSTITUTIONS |
|---|---|
| Gly | Ala |
| His | Asn; Gln |
| Ile | Leu; Val |
| Leu | Ile; Val |
| Lys | Arg |
| Met | Met; Leu; Tyr |
| Ser | Thr |
| Thr | Ser |
| Trp | Tyr |
| Tyr | Trp; Phe |
| Val | Ile; Leu |

Materials and Methods for the following Examples include the following:

Cell line K562: Source; American Type Culture Collection (ATCC), Rockville, Md. Isolation; Established by Lozzio and Lozzio (1975) from the pleural effusions of a female in blast crisis CML. This cell line contains multiple copies of the Ph$^1$ with breakpoint on chromosome 22 within the Mbcr (b3/a2 translocation). Cells are grown at 37° C. and 5% $CO_2$ in RPMI 1640 growth medium supplemented with 10% fetal calf serum (Gibco Laboratories, Grand Island, N.Y.).

Cell lines, SUP-B13 and SUP-B15: Source: Cell lines were generously provided by Steve D. Smith, Department of Pediatrics, University of Chicago. Isolation: Cell lines were obtained from the first and second bone marrow relapse samples, respectively, of an 8-yr-old male admitted to Children's Hospital at Stanford, Calif. in 1983 (Naumovski et al., 1988). Cell lines contain the Ph$^1$ chromosome with ALL specific breakpoint on chromosome 22 within the mbcr. However, these cell lines differ in the expression of some cell surface antigens rendering them related but unique. Cells are grown at 37° C. and 5% CO2 in RPMI 1640 growth medium supplemented with 20% fetal calf serum (Gibco Laboratories, Grand Island, N.Y.). Initial culture conditions require that these cells be grown in a six-well culture plate at optimum cell density, 0.5×10$^6$/ml, for 10–14 days. During this period, the cells must be counted daily to insure against overgrowth of the culture and the media must be replenished. The cells are then diluted to appropriate volumes with fresh culture media and the suspension aliquoted into the wells at approximately 6 mls of culture per well. After a sufficient number of wells have been seeded and culture remains healthy, the stocks are plated into T75 or T150 culture flasks for general growth. However, these cells are extremely fragile and appear to undergo a form of apoptosis or programmed cell death if the culture becomes either too dense or too dilute from optimal cell concentrations. This condition is immediately recognizable as the culture flask appears to be bacterially contaminated with small particles of cellular debris. This condition can be remedied by gentle centrifugation of the cell culture through 2 mls of fetal calf serum. The resulting cell pellet, free of cellular debris, is resuspended at appropriated cell concentrations in fresh culture media. Again, a careful monitoring on the status of this cell culture is required to insure proper cell viability.

Cell line SMS-SB: Source: R. Peter Gale, Los Angeles, Calif. Cells were isolated from the peripheral blood of a 17-yr-old female suffering from a relapse of lymphoblastic lymphoma. The cells synthesize but do not secrete u-chains and except for the lack of u-chain secretion, the phenotype of SMS-SB cells is the same as the major population of marrow pre-B cells (see Smith et al., 1981). Cells are cultured at 37° C. in 5% $CO_2$ in RPMI 1640 media supplemented with 10% fetal calf serum (Gibco Laboratories, Grand Island, N.Y.).

Cell line HL60: Source: American Type Culture Collection (ATCC), Rockville, Md. Isolation: Peripheral blood leukocytes were obtained from an adult female with acute promyelocytic leukemia. Most of the cells stained by the Wright-Giemsa procedure were myeloblasts and promyelocytes with azurophilic granules, but more mature myeloid cells were also seen (Collins et al., 1977). Cells are grown at 37° C. and 5% $CO_2$ in RPMI 1640 growth medium supplemented with 10% fetal calf serum (Gibco Laboratories, Grand Island, N.Y.).

Cell line M3.16: Source: The cells were provided generously by Dr. Pierre Laneuville at Hospital Royal Victoria Hospital in Montreal, Canada. Isolation: The IL3/GM-CSF-dependent cell line, designated M-07E cells was derived from an early passage of the primary culture from a patient with acute megakaryoblastic leukemia. M3.16 cell line was derived from M-07E cells that contain a retroviral vector that expresses P210 BCR-ABL. M3.16 cells grow without added IL3/GM-CSF in a DMEM/10%FCS (Sirard et al., 1994). Cells are grown at 37° C. and 5% $CO_2$ in DMEM supplemented with 10% fetal calf serum (Gibco Laboratories, Grand Island, N.Y.).

Cell line COS1: Source: ATCC (Rockville, Md). Isolation: COS1 is a fibroblast-like cell line established from simian kidney cells (CV1) that were transformed by an origin-defective mutant of SV40, which codes for wild-type T antigen. Cells were cultured in 37° C. and 5% $CO_2$ in DMEM supplemented with 10% fetal calf serum (Gibco Laboratories, Grand Island, N.Y.).

Plasmid Psp65 BCR: This plasmid was provided by Dr. John Groffen (Childrens Hospital of Los Angeles, Calif.). It is used for in vitro transcription (using SP6 polymerase) and translation.

Plasmid Psp65 c-ABL(1b) and Psp65/P210 BCR-ABL: These plasmids contain full length c-ABL(1b) or P210 BCR-ABL cDNAs, respectively. They were provided by Dr. Eli Canaani (Weissman Institute, Israel) and can be used for in vitro transcription (using SP6 polymerase) and translation.

Plasmid pSG5BCR: The original human full length BCR cDNAs were provided by Dr. John Groffen (Children's Hospital of Los Angeles, Calif.). The B3 clone that has the complete coding region of BCR plus about 150 bp 5' untranslated region was cloned into the EcoRI site of psp65 vector. The original human full length p210 BCR-ABL cDNA was obtained from Dr. Eli Canaani (The Weizmann Institute of Science, Israel). The p210 BCR-ABL construct, having the complete coding region plus about 10 bp 5' untranslated region, was positioned in the EcoRI/HindIII sites of psp65 vector. In order to reduce the 5' untranslated sequence of BCR for better expression, the EcoRI-XhoI fragment from p210 BCR-ABL was used to replace the EcoRI-XhoI fragment of the B3 clone. The newly constructed human full length BCR cDNAs containing about 10 bp 5' untranslated sequences were released from the psp65 vector by EcoRI digestion and subsequently inserted into the EcoRI site of an eucaryotic expression vector pSG5 (Stratagene, La Jolla, Calif.). The pSG5 vector contains the early SV40 promotor to facilitate in vivo expression in cells also expressing the T antigen.

Plasmid PSG5BCR-ABL: The human full length p210 BCR-ABL was released from the psp65 vector by EcoRI complete digestion and SacI partial digestion. The full length cDNA was then used to replace the EcoRI-SacI fragment of BCR in the pSG5 vector. This construct contains a large C-terminal BCR sequence after the stop codon of p210 BCR-ABL. Almost all of this C-terminal portion of the BCR sequence was removed by releasing a BamHI partial digested fragment.

Plasmid PSG5ABL(1b): The human full length p145 c-Abl(1b) cDNA was provided by Dr. Eli Canaani (The Weizmann Institute of Science, Israel). The c-Abl(1b) insert was released from psp65 vector by StuI (blunt end) partial digestion followed by EcoRI complete digestion. The EcoRI-StuI fragment was then ligated with PSG5 linearized by EcoRI and BalI (blunt end) digestion.

Figure 7:
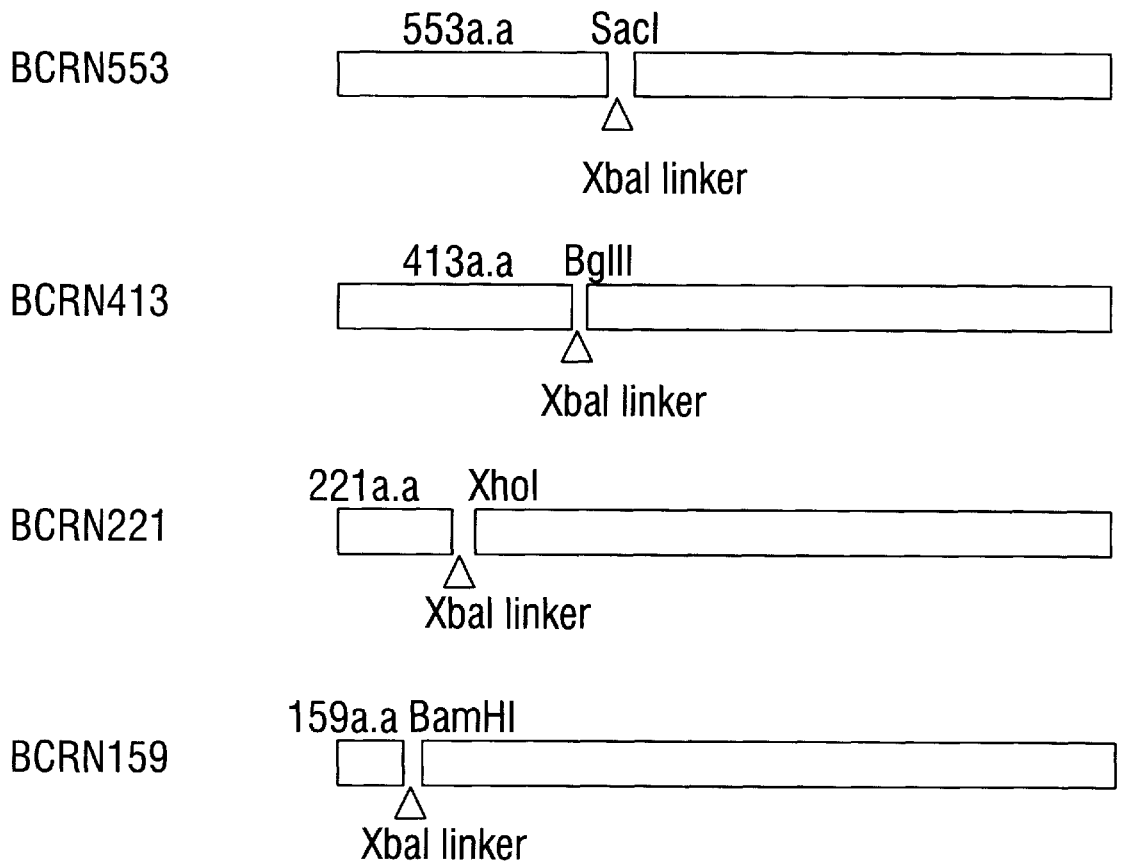
FIG. 7 provides a schematic diagram of the BCR deletion mutants.
Figure 8A:
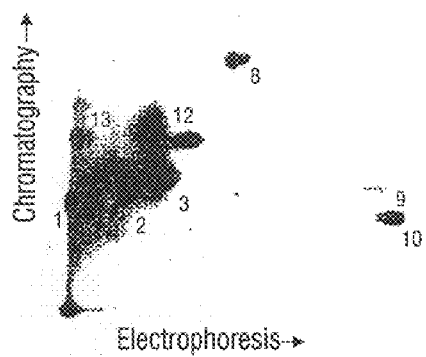
FIG. 8A–FIG. 8D (Scanned images) show two-D tryptic maps of in vitro phosphorylated Bcr-Abl proteins. Mutant and wild type Bcr-Abl proteins were expressed in COS-1 cells as described. Bcr-Abl proteins were phosphorylated in vitro using anti-Abl(52–64) immune complexes, and mapped. The dashed circles identify peptides lacking in the mutant.
Figure 8B:
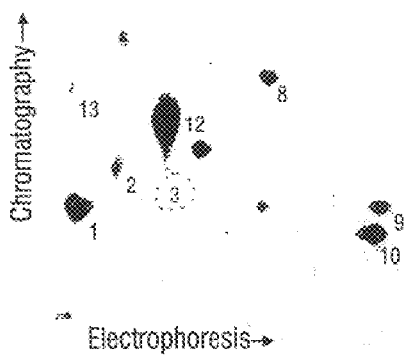
Figure 8C:
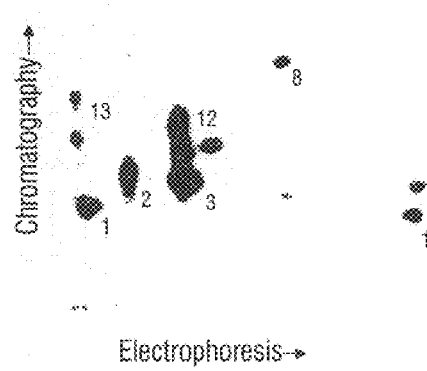
Figure 8D:
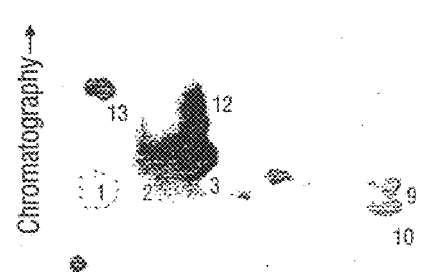

Plasmids PSG5BCRN553, PSG5BCRN413, PSG5BCRN221, PSG5BCRN159: These deletion mutants were obtained by inserting a XbaI linker containing stop codons at all three reading frames (CTAGTCTAGACTAG, SEQ ID NO:14, Stratagene, La Jolla, Calif.) into SacI, BglII, XhoI or BamHI site within the BCR first exon coding sequences, respectively (FIG. 7).

Site-Directed mutagenesis: Site-specific mutagenesis is a technique useful in the preparation of second generation proteins, or biologically functional equivalent proteins or peptides, derived from the sequences thereof, through specific mutagenesis of the underlying DNA. As noted above, such changes may be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17–25 nucleotides in length is preferred, with about 5 to 10 residues on both sides of the junction of the sequence being altered.

In general, the technique of site-specific mutagenesis is well known in the art, as exemplified by Adelman et al., (1982). As will be appreciated, the technique typically employs a phage vector which exist in both a single stranded and double stranded form. Typical vectors useful in site-directed mutagenesis include vectors such as the M13 phage (Messing et al., 1981). These phage are commercially available, and its use is generally known to those of skill in the art.

In general, site-directed mutagenesis in accordance herewith is performed by first obtaining a single-stranded vector which includes within its sequence a DNA sequence which encodes all or a portion of the Bcr-Abl polypeptide sequence selected. An oligonucleotide primer bearing the desired mutated sequence is prepared, generally synthetically, for example, by the method of Crea et al., (1978). This primer is then annealed with the singled-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as E. coli cells, and clones are selected which include recombinant vectors bearing the mutated sequence arrangement.

P185 BCR-ABL and p160 BCR constructs with Tyr to Phe mutations at residues 177 and 360 of BCR were supplied by Dr. Groffen's group (Childrens Hospital of Los Angeles, Calif.). Other mutations were first made in the wild type BCR by the method described below. p210 BCR-ABL mutants were then obtained by exchanging XhoI/SacI fragments of wild type p210 BCR-ABL with the same fragment from the mutant p160 BCR.

The TRANSFORMER™ Site-Directed Mutagenesis Kit (CloneTech Laboratories, Palo Alto, Calif.) was used for generating Tyr to Phe mutants. The mutagenic primers used for mutating tyrosine residues within BCR first exon were obtained from Operon Technologies (Alameda, Calif.), and their sequences are listed below.

| Tyrosine residue | Mutagenic primer | |
|---|---|---|
| 276 | 5' CCCCTGGAGTTCCAGCCCTAC 3' | SEQ ID NO:15 |
| 283 | 5' CAGAGCATCTTCGTCGGGGGC 3' | SEQ ID NO:16 |
| 316 | 5' CGCAGGTCCTTCTCCCCCCGG 3' | SEQ ID NO:17 |
| 328 | 5' GGAGGCGGCTTTACCCCGGAC 3' | SEQ ID NO:18 |

These mutagenic primers are used to mutate tyrosine to phenylalanine. The selection primer (5' TGGTC-GACTCGCGACTCTTCC 3' (SEQ ID NO:19)) for mutagenesis on pSG5BCR constructs was used to eliminate a unique restriction site XbaI in the vector pSG5. All of the mutations were verified by direct sequencing of the mutagenized regions.

Immunokinase Assay

The immunokinase assays were performed as described by Campbell et al. (1990) with modifications. The cells are lysed by homogenizing the cell pellet in two different lysis buffers at 0° C. in a tight fitting Wheaton homogenizer (either 0.1% Triton-X100, 100 mM NaCl, 5 mM EDTA, 10 mM sodium phosphate, pH 7.2 or 1% Triton-X100, 100 mM NaCl, 0.5 sodium deoxycholate, 0.1% SDS, 5 mM EDTA, 10 mM sodium phosphate pH 7.2). Both buffers were supplemented with 30 mM sodium pyrophosphate, 100 KIU aprotinin, 1 mM benzamidine, 1 mM phenylmethylsulfonyl fluoride and 0.2 mM sodium vanadate. The cell lysate was then clarified by centrifugation at 100,000×G for 30–60 minutes at 4° C. The clarified supernatant was collected and divided equally among the samples for immunoprecipitation. Immunoprecipitation reactions were carried out utilizing 20–40 μl of the respective anti-peptide rabbit sera or 5 μl of monoclonal antibody at 0° C. for 1 hour. Blocked immunoprecipitations refer to those immunoprecipitation reactions performed with antisera that have been preincubated with excess cognate peptide to specifically block the anti-peptide antibodies. The resulting antigen-antibody immunoprecipitates were collected with 30 μl of 50% protein A-Sepharose (Pharmacia, Uppsala, Sweden), pelleted and washed with RIPA buffer (0.1% Triton X-100, 0.05% SDS, 0.5% sodium deoxycholate, 100 mM NaCl in 10 mM phosphate buffer, pH 7.2), wash buffer (0.1% Triton X-100, 100 mM NaCl, in 10 mM phosphate buffer, pH 7.2) and finally with 50 mM Tris buffer, pH 7.2. The immunoprecipitate pellet was suspended in 50 μl of kinase assay buffer (100 mM NaCl, 0.1% Triton X-100, 10 mM $MnCl_2$ in 20 mM HEPES buffer pH 7.2) containing 0.02 mCi [gamma-$^{32}$P] adenosine triphosphate for 10 minutes at 0° C. The labeled pellets were washed once in RIPA buffer and then denatured by boiling in mercaptoethanol/sodium dodecyl sulfate (SDS) sample buffer (1% SDS, 10% 2-mercaptoethanol, 10% glycerol, 1 mM EDTA, in pH 8.0 Tris buffer). The boiled supernatant was resolved by SDS polyacrylamide gel electrophoresis (PAGE) on a 6.5% polyacrylamide gel. The dried gel was exposed to X-ray film using enhancing screens.

Immunoblotting Assays

Cells were lysed in Laemmli sodium dodecyl sulfate (SDS) sample buffer containing 10% 2-mercaptoethanol. The lysates were boiled for 3 minutes and then clarified by centrifugation at 100,000×g for 1 hour at room temperature. The supernatant fluid was collected and allocated. The samples were resolved by SDS polyacrylamide gel electrophoresis (PAGE). The gels were electroblotted onto Immobilon P membranes (Millipore Corp., Bedford, Mass.) at 4° C. in transfer buffer (192 mM glycine, 25 mM Tris-HCl, pH 7.5, and 1% methanol) for 4–5 hours at 1.2 amps. Blots were blocked by washing in 1–3% bovine serum albumin (BSA) in washing buffer (150 mM NaCl, 0.1% NONADET™ P40, 50 mM Tris-HCl, pH 7.5 or 0.01M Tris, pH 7.5, 0.1 M NaCl, 0.1% TWEEN™ 20) or 10% nonfat milk in washing buffer (20 mM Tris-HCl base, pH 7.6, 137 mM NaCl, 3.8 mM HCl and 0.1% TWEEN™ 20) for 1–2 hours at 37° C. The filters were then reacted with antibodies of appropriate dilution (1:20,000 for 8E9; 1:1,000 for anti-peptide antibodies; 1:250 for anti-Grb2 antibody; 1:1,000–2,500 for anti-phosphotyrosine antibodies) in blocking buffer 2 hours at room temperature or overnight at 4° C. The filters were washed in washing buffer and scored with $I^{125}$-protein A (Amersham Co., Arlington Hts., Ill.) directly for rabbit antibody or mixed with rabbit anti-mouse IgG for monoclonal antibody (1 μg/10 uCi of $I^{25}$-protein A) for 1 hr at room temperature in blocking buffer. Filters were washed in washing buffer, air dried and exposed to X-ray film. An alternative method is to incubate the filters with horseradish peroxidase coupled anti-rabbit or anti-mouse Ig and then react with ECL reagents (Amersham Co., Arlington Hts., Ill.) after washing with washing buffer. The signals are detected by exposing the filters to hyperfilm (Amersham).

Tryptic Peptide Mapping of Phosphopeptides $^{32}$P labeled proteins from in vitro kinase assays were resolved by electrophoresis on a SDS-6.5% PAGE gel. After electrophoresis, the gel was dried and autoradiographed with Kodak RP-1 X-ray film. The $^{32}$P-labeled proteins were excised from the dried gel using the autoradiograph as a template. The blocking paper was scraped from the dried gel bands that were cut into small pieces and allowed to swell in a volume of elution buffer (0.05M $NH_4CO_3$, pH 8.5, 0.1% SDS, 0.5% 2-mercaptoethanol) corresponding to 2 ml buffer/1 $cm^2$ dried gel. The swollen gel pieces were further crushed with a glass stir rod. The homogenate solution was boiled for 5 min and shaken overnight at 37° C. in a rotating wheel mixer to elute the labeled protein. The gel fragments were pelleted by centrifugation at 10,000×G for 10 min and the supernatant fluid carefully decanted and saved. A volume of fresh elution buffer at half the initial volume was then added to the gel fragments and this solution mixed at 37° C. for 4 hours as before. The gel fragments were pelleted again by centrifugation and the supernatant fluid decanted and saved. The elution fractions were pooled and the combined eluate filtered through a 0.2μ pore size millipore syringe filter. Bovine serum albumin (75 μg) was added to the eluate and mixed thoroughly. The BSA carrier and eluted $^{32}$P labeled protein was pelleted by making the solution 20% in trichloroacetic acid and incubating on ice for 4 hr. The precipitated protein was pelleted by centrifugation, washed successively with ice-cold ethanol followed by an ice-cold solution of ethanol: ether (1:1) and the washed pellet centrifuged and air dried. The dried protein pellet was dissolved in 150 μl of chilled performic acid (30% $H_2O_2$ and 98% formic acid [1:9]) previously incubated for 1 hr at room temperature and incubated for 2 hr. at 0° C. The performic acid oxidizing solution was diluted with water and lyophilized on a speed vacuum dryer. The resulting oxidized protein was digested with 30 μg of L-(1-tosylamido-2-phenyl) ethyl choromethyl ketone-treated trypsin (TPCK trypsin) in 0.5 ml of 0.05 M $NH_4HCO_3$ for 18 hr at room temperature. After 28 hr, an additional 20 μg of TPCK trypsin was added to the solution and the digestion continued for an additional 4 hrs.

The digested protein was diluted with water and lyophilized repeatedly until the $NH_4HCO_3$ salt was removed. The salt-free digest was dissolved in 15 μl of pH 2.1 electrophoresis buffer (distilled water, formic acid and acetic acid [90:2:8], pH 2.1) and applied as a spot to cellulose thin layer plate (Kodak #13255, Rochester, N.Y.) and electrophoresed for 1 hr at 1000V on a Hunter systems electrophoretic unit (HTLE 7000, CBS Scientific Co., Del Mar, Calif.). Following electrophoresis, the plate was air dried and chromatographed in a thing-layer chromatography tank using a chromatography buffer consisting of N-butanol, acetic acid, water and pyridine [75:15:60:50]. The chromatography was run until the chromatography buffer had run the length of the plate or approximately four hours.

Phosphoamino acid analysis of tryptic peptides was accomplished by carefully removing the labeled tryptic peptide from the chromatography plate by scraping the cellulose matrix using the autoradiograph as a template. The labeled tryptic peptide was eluted from the cellulose matrix with 20% acetonitrile and treated with 6N HCl for 90 min at 110° C. The clarified supernatant fluid was fractionated on thin layer plates (Chromogram without fluorescent indicator, Eastman Kodak, Rochester, N.Y.) in the presence of standard phosphoserine, phosphothreonine and phosphotyrosine. Radioactive phosphoamino acids were detected by autoradiography and the position of the standard phosphoamino acids detected by ninhydrin treatment.

V8 protease digestion $^{32}$P labeled protein bands were cut out from a polyacrylamide gel and rehydrated with buffer A (0.125M Tris-HCl, pH 6.8, 0.1% SDS, and 1 mM EDTA). The gel slice was loaded into the wells of a 10.5% polyacrylamide gel and the wells were covered with buffer A containing 20% glycerol and 1 μg V8 protease. The gel was then run at 20 mA for 20 mins and stopped for 30 min. After that, electrophoresis continued.

An acceptable protocol for standard human bone marrow transplant has already been established in the medical arts and is thus an available technique to those of ordinary skill in the art. The described peptide mixture or retroviral pre-treated and processed bone marrow samples, as described by the inventors, create an improved anti-cancer therapeutic regimen which could be readily implemented into standard bone marrow transplant techniques by the clinician in the treatment of leukemia patients.

As part of a total therapeutic regimen for the clinical management of the leukemic patient, the present invention can be used to effect an at least a 2-log (100×) reduction in the ratio of normal cells to leukemic cells in any particular bone marrow sample. Upon transplantation into a patient as part of a bone marrow transplant, it is expected that an at least 2–3-log overall reduction in the ratio of leukemic cells to normal cells in the patient may be provided. While the present technique may not accommodate the entire population of patients afflicted with CML (because of the small percentage of CML patients eligible for allogenic bone marrow transplantation due to advanced age (i.e., a chronological age of greater than 50 at most medical centers) or availability of donors (25% of 30% of patients with CML have donors)), it nonetheless is postulated to provide a marked improvement in the overall effectiveness of bone marrow transplant procedures for treating leukemic patients compared to those with non-pre-treated bone marrow samples currently employed.

A listing of some of the peptides useful in various applications of the invention are provided in the following table.

TABLE A

| Peptide | SEQ ID NO | Fragments |
|---|---|---|
| 1. 1–426 Bcr (first exon) | 1 | as described below |
| 2. 1–63 Bcr | 2 | 18–68, 28–68 |
| 3. 1–71 Bcr | 3 | 25–71, 28–68 |
| 4. 28–58 Bcr | 4 | 22–60, 26–63 |
| 5. 1–159 Bcr | 5 | 28–68, 28–159 |
| 6. 1–221 Bcr | 6 | 28–68, 1–159, 28–159, 28–221 |
| 7. 1–413 Bcr | 7 | 28–68, 1–159, 1–221, 28–413 |
| 8. 164–181 Bcr | 8 | 176–180, 168–180 |
| 9. 314–320 Bcr | 9 | |
| 10. 353–364 Bcr | 10 | 359–363, 353–365 |
| 11. 255–293 Bcr (peptide #3) | 11 | 278–285, 278–290 |
| 12. 637–644 Bcr (peptide #8) | 12 | 640–644, 635–645 |

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Bcr Peptides for Inhibition of Coiled Coil Interaction Between Bcr-Abl Molecules to Prevent Oligomerization The present invention provides methods that employ compositions comprising peptides having sequences from the N-terminal region of the Bcr portion of Bcr-Abl. These peptides inhibit a coiled-coil interaction between the Bcr portion of Bcr-Abl monomers, an interaction that is involved in formation of the tetrameric active form of Bcr-Abl. An excess of these N-terminal peptides will prevent tetramer formation and, thereby, prevent autophosphorylation of Bcr-Abl and its subsequent oncogenic functions. SEQ ID NO:1 provides the amino acid sequence of the first exon of Bcr.

These N-terminal peptides may have the sequence of amino acids 1–63 (SEQ ID NO:2), or amino acids 1–71 (SEQ ID NO:3), or amino acids 28–58 (SEQ ID NO:4), or amino acids 1–159 (SEQ ID NO:5), or amino acids 1–221 (SEQ ID NO:6) or amino acids 1–413 (SEQ ID NO:7) or equivalents thereof. These peptides having less than about 45 amino acid residues will be chemically synthesized by the solid phase method of Merrifield (15), which reference is specifically incorporated by reference herein, using an automatic peptide synthesizer (Vega DuPont, Wilmington, Del.), with standard t-butoxycarbonyl (t-Boc) chemistry that is well known to one skilled in this art in light of this disclosure. The amino acid composition of the synthesized peptides will be determined by amino acid analysis with a Waters Pico-tag analyzer, (Medford, Mass.) to confirm that they correspond to the expected compositions. The purity of the peptides will be determined by sequence analysis or HPLC. These peptides will then be used to examine the inhibition of Bcr-Abl oligomerization.

These peptide sequences may be expressed by way of a recombinant retrovirus vector, and, a preferred method of delivery for peptides greater than about 45 amino acids is a recombinant retrovirus vector. Using a retrovirus vector that can infect bone marrow cells of patients, a fragment of the BCR gene encoding a 159 amino acid amino terminal fragment of Bcr would be introduced into bone marrow. Since normal Bcr protein forms a stable complex with Bcr-Abl, overexpression of Bcr 159 would be expected to generate heterotetrameric structures composed of one molecule of Bcr-Abl and three molecules of Bcr 159. The tetramer should be inactive as a tyrosine kinase not only for autophosphorylation of Bcr-Abl but also inactive as a kinase to phosphorylate substrates such as Shc and Crkl.

EXAMPLE 2

Bcr-Abl Peptides that Bind Adapter Proteins

The present inventors provide herein sets of adapter protein-Bcr peptide pairs that demonstrate binding affinity for each other. Therefore, these Bcr peptides, when provided in excess, would bind their respective binding sites on the adapter protein and prevent the adapter protein from interacting with endogenous Bcr-Abl. This interaction prevents the adapter protein from effecting its role in signal transduction, most particularly, in the Ras activation pathway. The peptides may be provided in a phosphorylated form or a nonphosphorylated form. Phosphorylation is expected to occur within the cell; the form of the peptide that binds to the adaptor protein is the phosphorylated form.

The adapter protein-Bcr peptide pairs provided by the present invention are: Bcr peptide 164–181 containing $pY^{177}$ (SEQ ID NO:8) (or at least a 4-mer fragment thereof, such as Bcr 176–180, such as a 12-mer, for example, a 12-mer peptide corresponding to 168–180 Bcr), and adapter protein Grb2/mSos1; SH3 domain of Abl and adapter protein Shc; Abl peptide and adapter protein Crkl; and Bcr peptide 353–364 (SEQ ID NO:10) (or at least a 4-mer fragment thereof, such as Bcr 359–363, such as a 12 mer, for example, Bcr 353–365) and an adapter SH2-containing protein.

A preferred peptide combination of the present invention is a set of peptides or a polypeptide having sequences from Bcr that include $Y^{177}$, $Y^{283}$ and $Y^{360}$, such as, for example, the peptide of SEQ ID NOS:8, 10 and 11. A peptide including this set of binding sites should be at least 3 or 4 amino acids long, and optimally be 10 or 12 or 15 amino acids long. The tyrosine is about in the middle of the peptide since sequences to the carboxy-terminal side may be especially important for peptide binding, e.g., Asn 179 of the peptide that contains $Y^{177}$. A polypeptide containing these sequences would have spacer amino acids to allow flexibility of the molecule for optimum binding. The peptides of the present invention are preferably provided with amino-terminal acetyl groups so as to block the $NH_2$-terminal end from protease degradation and with an amide group at the carboxy terminal end. Acetylation of the amino terminal end is accomplished using acetic anhydride following completion of the peptide. The acetylation is done on the nascent peptide bound to the resin. The carboxy-terminal amide is accomplished by beginning the synthesis of the peptide onto derivatized resin (i.e., PAL Support; Millipore #GEN077483; Medford, Mass.). When the peptide is removed from this type of resin, it will have an amide group at its C-terminus.

Bcr peptide 164–181 (SEQ ID NO:8) and adapter protein Grb2/mSos1: The Bcr binding site within Bcr-Abl has been identified by the inventors. The following Bcr peptide sequence binds the SH2 domain of Grb2: GHGQPGADAEKPFpY$^{177}$VNVE (residues 164–181) (SEQ ID NO: 8). The tyrosine residue at position 177 is phosphorylated by the Abl tyrosine kinase within Bcr-Abl.

SH3 domain of Abl, and adapter protein Shc: The SH3 domain of Abl contains a sequence that is expected to bind a proline-rich sequence of Shc.

Abl peptide, and adapter protein Crkl: Crk (related to Crkl) is phosphorylated on $Y^{221}$ by p145Abl. CRKL is expected to be a biologically significant substrate for Bcr/Abl. One of the SH3 domains of CRKL is expected to bind to a proline-rich sequence within the Abl domain of Bcr-Abl.

Ecr peptide 353–364 (SEQ ID NO:10) and an SH2 domain of an adapter protein. Another phosphotyrosine peptide within Bcr, VSPSPTTpY$^{360}$RMFR, SEQ ID NO:10, (residues 353–364) is also involved in binding of an adapter SH2-containing protein. This sequence surrounds tyrosine 360 of Bcr and $Y^{360}$ is also phosphorylated by the Abl tyrosine kinase within Bcr-Abl.

EXAMPLE 3

Peptide 255–293 Mutation Studies

Figure 10A:
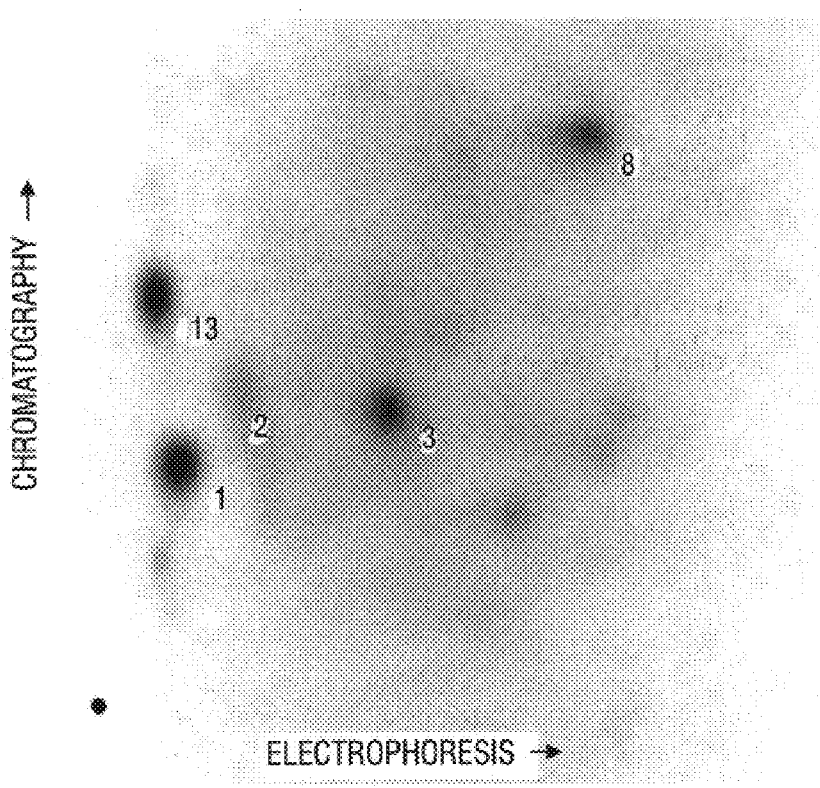
FIG. 10A and FIG. 10B (Scanned images) show an absorbed tryptic map of p210. GST-Abl SH2 binds phosphotyrosine tryptic peptide 3, which contains tyrosine 283. p210 Bcr-Abl labeled in the in vitro kinase assay from K562 cells was purified on SDS gels, digested with trypsin and the digest was split in two parts. One was absorbed with GST (FIG. 10A) and the other with GST-Abl SH2 (FIG. 10B). The peptides that did not bind to the beads were separated on thin layer plates as usual. The dashed circles identify peptides lacking in the GST-Abl SH2 absorbed fractions.
Figure 10B:
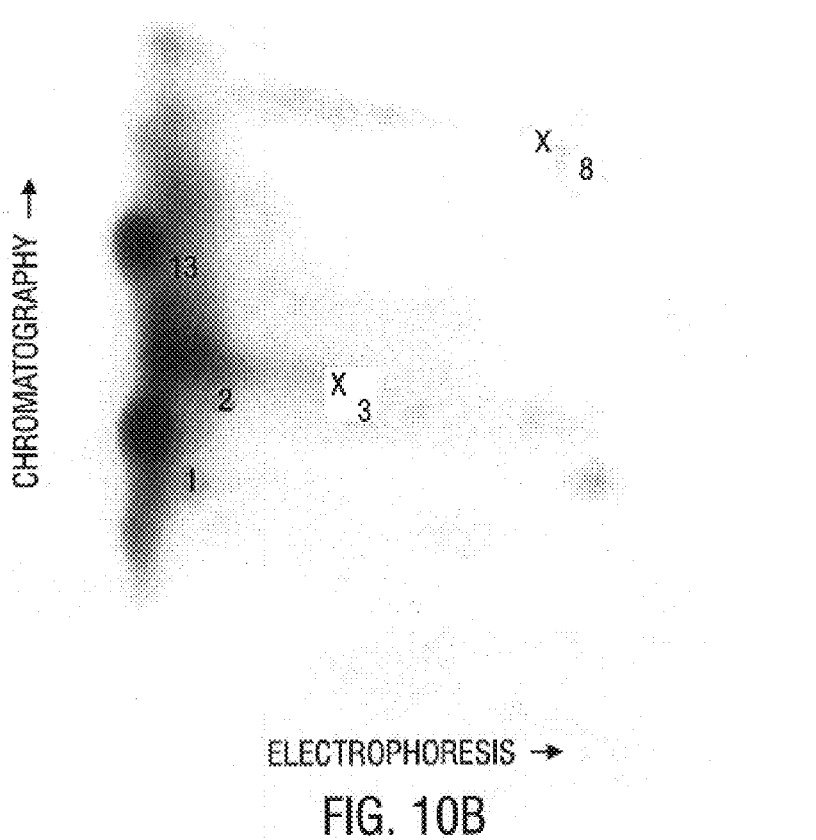

The present inventor has conducted studies in which the amino terminal SH2 domain of Ras Gap was expressed as a fusion protein containing the glutathione S transferase protein (GST). These experiments involve mixing GST-Gap SH2 with phosphotyrosine tryptic peptides of Bcr-Abl. Spots #3 and #8 specifically bound to the GST-Ras Gap SH2 fusion protein, but not to GST (FIG. 10A AND 10B). Spot #3 contains a peptide designated 255–293 (SEQ ID NO:11) having tyrosines 283, 279 and 276 (not phosphorylated). Tyrosine 283 is not involved in binding Ras Gap. Therefore, tyrosine residue 279 is likely to be part of the peptide of Bcr that binds Ras Gap. The sequence 255–293 (SEQ ID NO:11) binds Ras Gap and an SH2 domain of Abl. Fragments of this peptide that include at least Bcr 278–284 or Bcr 278–282, such as a Bcr 278–290 12 mer, are expected to provide useful peptides for inhibition of Bcr-Abl.

A further tyrosine at position 283 (residues 255–293, SEQ ID NO:11) is also phosphorylated by the Abl tyrosine kinase within Bcr-Abl. Several other tyrosines within Bcr are also phosphorylated by Bcr-Abl. They are likely to be $Y^{70}$ and $Y^{279}$, or possibly tyrosine at positions 58, 231 or 246. $Y^{276}$, $Y^{316}$ and $Y^{328}$ appear not to be sites of phosphorylation.

EXAMPLE 4

Abl SH2 Domain Binds to a Bcr Peptide Within the First Exon of Bcr-Abl

The present inventors performed similar studies as described in Example 3 with the SH2 domain of Abl. These were performed with a mouse c-Abl SH2 sequence, which differs by only two amino acids from the human sequence within the SH2 domain. The results indicate that phosphotyrosine tryptic peptides #3 and #8 bind to GST-Abl SH2 but not to GST (FIG. 10A and 10B). It is not known why Ras Gap SH2 and Abl SH2 bind the very same phosphotyrosine tryptic peptides. The sequence of peptide 8 is 637 NSLETL-LYK 644, (SEQ ID NO:12), its position is outside of the first exon (it is lacking in p185 Bcr-Abl but present in p210 Bcr-Abl; the former contains only the first exon of Bcr whereas the latter contains more than 900 amino acids of Bcr.) Peptide #3 has the sequence of amino acids 255 FL KDNLIDANGGS RPPWPPLEYQPYQSIYVGGMMEGEGK 293 (SEQ ID NO:11, the underlined residues are sites resistant to trypsin).

The following study was carried out to demonstrate that tyrosine 177 phosphorylated p160 Bcr binds to a simian Grb2 molecule, an activator of the Ras signaling pathway.

It has been shown that phosphotyrosine 177 of Bcr sequences within Bcr-Abl is required for its direct interaction with SH2 domain of Grb2, an SH2 and SH3 domain-containing adaptor molecule[3]. The interaction is important for activation of Ras function and transformation by Bcr-Abl[3]. p210 Bcr-Abl can transphosphorylate p160 Bcr on tyrosine 177, it was of interest to test whether tyrosine 177 phosphorylated p160 Bcr might also be able to bind to Grb2 protein within cells. Searching for such a complex would be difficult in cells that express both p210 Bcr-Abl and p160 BCR since p210 Bcr-Abl will interact with both p160 Bcr and Grb2 proteins. In order to demonstrate direct interaction between tyrosine phosphorylated p160 Bcr and Grb2 proteins, it would be reasonable to take the advantage of the facts that p160 ECR can be tyrosine phosphorylated by p146 c-Abl and the lack of physical interaction of p145 c-ABL with either p160 Bcr or Grb2.

Figure 18:
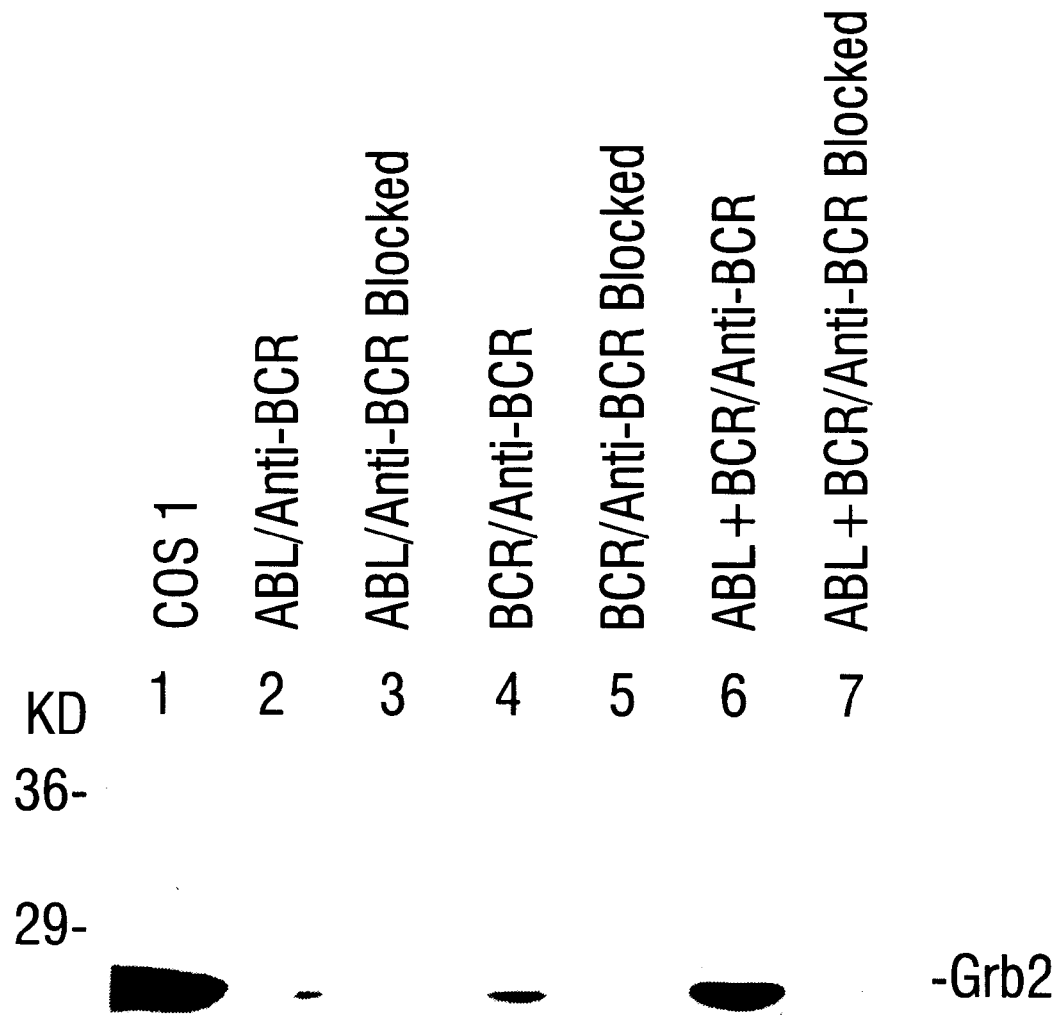
FIG. 18 (Scanned image) shows physical interaction of tyrosine phosphorylated p160 BCR with simian Grb2 protein in COS1 cells overexpressing both p160 BCR and p145 c-ABL. Anti-Grb2 Western blotting was performed on lysates of COS1 cell lysates (lane 1) or anti-BCR (1256–1271) antibody immunoprecipitates from COS1 cells transfected with human full length c-ABL (1b) (lanes 2 and 3), human full length Bcr (lanes 4 and 5) or cotransfected both human full length Bcr and c-ABl(1b) (lanes 6 and 7). Lane 3, 5 and 7 are immunoprecipitates obtained with pre-blocked anti-BCR (1256–1271) antibody. The bands were detected using the ECL method. Exposure time: 30 seconds.

COS1 cells express an endogenous simian Grb2 protein detected by Western blotting (FIG. 18, lane 1). P160 BCR and p145 c-ABL(1b) were separately or simultaneously expressed in COS1 cells. Two days after transfection, cells were harvested. The cell lysates were clarified by ultracentrifugation and the supernatants were incubated with either anti-BCR c-terminal (1256–1271) antibody (FIG. 18, lanes 2, 4 and 6) or peptide preblocked antibody (FIG. 18, lanes 3, 5 and 7). The immunoprecipitated proteins were then fractionated by a 10% polyacrylamide SDS PAGE and then transferred to a p-immoblin membrane. The membrane was then blotted by an anti-Grb2 antibody (FIG. 18). The result showed that Grb2 protein can be specifically co-immunoprecipitated with tyrosine phosphorylated p160 BCR by anti-BCR c-terminal (1256–1271) antibody from COS1 cells overexpressing both p160 BCR and p145 c-ABL (1b) (compare FIG. 18, lanes 6 and 7). However, expression of either p160 BCR alone (FIG. 18, lanes 2 an d3) or p145 c-ABL alone (FIG. 18, lanes 4 and 5) did not result in significantly specific co-immunoprecipitation of Grb2 protein by anti-BCR c-terminal (1256–1271) antibody. The weakly blocked 24 kd protein bands are likely resulted form non-specific immunoprecipitation of simian Grb2 molecule by the polyclonal anti-BCR c-terminal (1256–1271) rabbit serum and the presence of low amount of tyrosine phosphorylated endogenous BCR protein. The results indicate that p160 BCR when tyrosine phosphorylated by p145 c-ABL can interact with the endogenous similar Grb2 protein.

Figure 19:
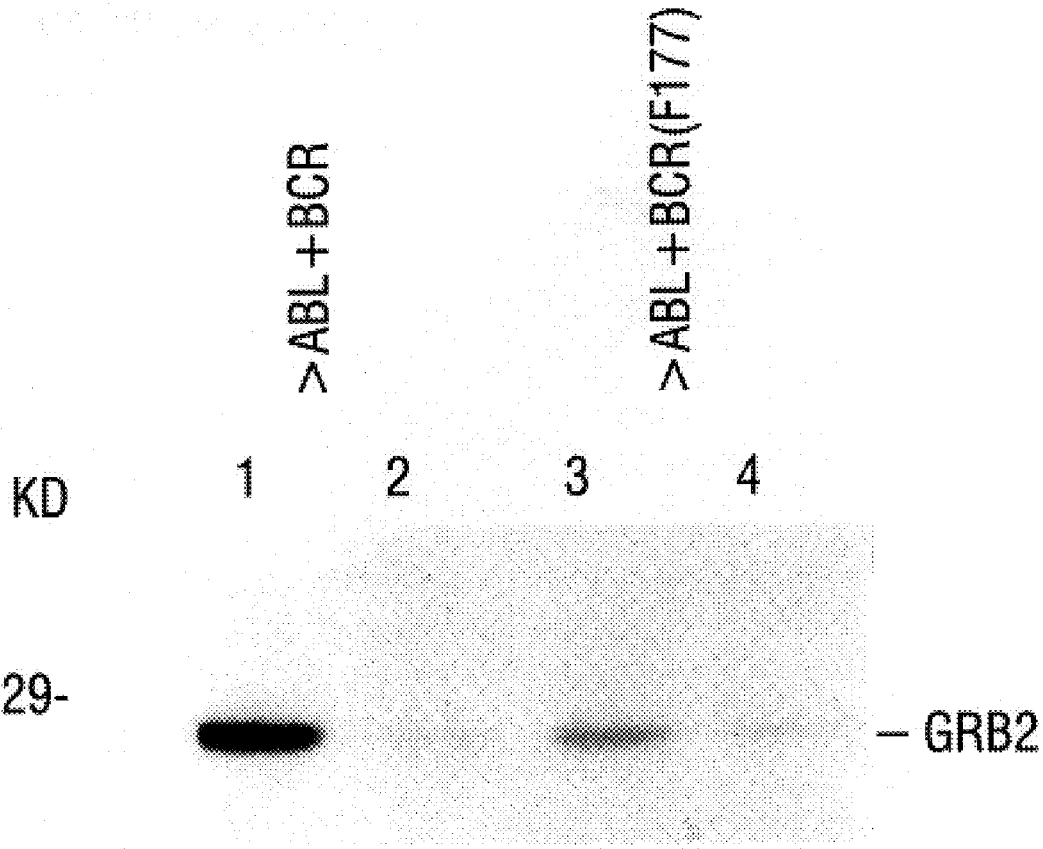
FIG. 19 (Scanned image) shows phosphotyrosine 177 of p160 BCR is critical for its interaction with the simian Grb2 protein. Anti-Grb2 Western blotting was performed on anti-BCR (1256–1271) antibody immunoprecipitates of lysates from COS1 cells cotransfected p145 c-ABL with either wild type p160 BCR (lanes 1 and 2) or p160 BCR (F177) (lanes 3 and 4) mutant. Lanes 2 and 4 are immunoprecipitation with pre-blocked anti-BCR (1256–1271) antibody.

In order to determine whether phosphorylation of tyrosine 177 of p160 BCR by p145 c-ABL(1b) is responsible for the interaction of p160 BCR with simian Grb2 protein, the Grb2 binding ability of tyrosine 177 to phenylalanine mutant of p160 BCR was tested. In this experiment, p145 c-ABL was coexpressed with either wild type p160 BCR or the mutant p160 BCR(F177) in COS1 cells. Cell lysates were subjected to immunoprecipitation ;by anti-BCR C-terminal (1256–1271) antibody and the immunoprecipitates were analyzed by Western blotting with an anti-Grb2 antibody. As expected, tyrosine phosphorylated wild type p160 PCR by p145 c-ABL(1b) was able to bind specifically to simian Grb2 proteins (compare lanes 1 and 2 of FIG. 19). However, coexpression of p145 c-ABL(1b) with p160 BCR lacking tyrosine 177 in COS1 cells resulted in a much reduced level of coimmunoprecipitate simian Grb2 protein by anti-BCR C-terminal (1256–1271) antibody (compare lanes 3 and 4 of FIG. 19 to lanes 1 and 2). This weak coimmunoprecipitation observed in lane 3 and 4 of FIG. 19 is likely resulted from non-specific immunoprecipitation by the anti-GBCR (1256–1271) antibody and the presence of endogenous wild type BCR. These results indicate that not only phosphotyrosine 177 of Bcr-Abl but also phosphotyrosine 177 of p160 BCR are able to bind to Grb2 proteins. It also implicated that normal c-Abl protein, when activated, may activate Ras pathway through phosphorylation of tyrosine 177 of p160 BCR.

EXAMPLE 5

Bcr-Abl Peptides as Standards for Radioiodination

The Bcr/Abl peptides of the present invention having a tyrosine residue are provided as standards for radioiodination. The tyrosine-containing peptides are at least about 3–4 amino acids long, preferably 10–12 amino acids long and may be 14–16 or more amino acids long. These peptides are useful as controls for testing the efficiency of radioiodinating a test peptide or protein by comparing the specific radioactivities of the test radioiodinated peptide or protein to a radioiodinated peptide of the present invention.

Radioiodination of proteins is discussed in Bailey, G. S., *Methods in Molecular Biology* 1. *Proteins,* Ed. J. M. Walker, Humana Press, Clifton, N.J. 1984, pp 325–333, which reference is incorporated by reference herein. Radioiodinated molecules are of major importance in studies of intermediary metabolism, in determinations of agonist and antagonist binding to receptors, and in quantitative measurements of physiologically active molecules in tissues and biological fluids, for example. In those studies, it is necessary to measure very low concentrations of the particular substance, and that requires a radioactively labeled tracer molecule of high specific radioactivity. Such tracers, particularly in the case of peptides and proteins, are conveniently produced by radioiodination.

Two τ-emitting radioisotopes of iodine are widely available, $^{125}$I and $^{131}$I. As τ-emitters they can be counted directly in a τ counter without the need for sample preparation, which is in direct contrast to β-emitting radionuclides, such as $^3$H and $^{14}$C. The counting efficiency for $^{125}$I is approximately twice that for $^{131}$I. Thus, in most circumstances, $^{125}$I is the radionuclide of choice for radioiodination.

Several different methods of radioiodination of proteins have been developed (Bolton, A. E. (1977) "Radioiodination Techniques" Amersham International, Amersham, Bucks, England.). They differ primarily in the nature of the oxidizing agent for converting $^{125}$I$^-$ into the reactive species $^{125}$I$_2$ or $^{125}$I$^+$. Those reactive species substitute into tyrosine residues of the protein, but substitution into other residues, such as histidine, cysteine, and tryptophan, can occur.

The chloramine-T method, developed by Hunter and Greenwood (Nature 194, 495–496, 1962), is a commonly used technique for protein or peptide radioiodination. It is a straightforward method in which the radioactive iodide is oxidized by chloramine-T in aqueous solution. The oxidation is stopped after a brief period of time by addition of excess reductant. Some proteins or peptides are denatured under the relatively strong oxidizing conditions, and so other methods of radioiodination that employ more gentle conditions have been devised, e.g., the lactoperoxidase method (Marchalonis, J. J. *Biochem. J.* 113, 299–305, 1969).

Materials:

1. Na$^{125}$I: 1 mCi, concentration 100 mCi/mL.
2. Buffer A: 0.5M sodium phosphate buffer, pH 7.4.
3. Buffer B: 0.05M sodium phosphate buffer, pH 7.4.
4. Buffer C: 0.01M sodium phosphate buffer containing 1M sodium chloride, 01% bovine serum albumin, and 1% potassium iodide, final pH 7.4.
5. Chloramine-T solution: A 2 mg/mL solution in buffer B is made just prior to use.
6. Reductant: A 1 mg/mL solution of sodium metabisulfite in buffer C is made just prior to use.
7. Protein or peptide to be iodinated: A 0.5–2.5 mg/mL solution is made in buffer B.

Method:

1. Into a small plastic test tube (1×5.5 cm) are added successively the protein or peptide to be iodinated (10 μg), radioactive iodide (5 μL), buffer A (50 μL), and chloramine-T solution (25 μL).
2. After mixing by gentle shaking, the solution is allowed to stand for 30 s to allow radioiodination to take place.
3. Sodium metabisulfite solution (500 μL) is added to stop the radioiodination and the resultant solution is mixed. It is then ready for purification.

Purification of Radioiodinated Protein or Peptide: For most uses of radioiodinated proteins or peptides, it is desirable to have the labeled species as pure as possible with the constraints, however, that the purification is achieved as rapidly as possible. For that purpose the most widely used of all separation techniques is gel filtration. Various types of Sephadex resin can be employed, e.g., G-50, G-75 and G-100 depending on the differences in sizes of the molecules present in the mixture.

Typically the mixture is applied to a column (1×25 cm) of Sephadex resin and is eluted with 0.05 M sodium phosphate buffer of pH 7.4 containing 0.15 M sodium chloride and 0.1% bovine serum albumin. Fractions (0.5–1.0 mL) are collected in plastic tubes and aliquots (10 μL) are counted. Using those results, an elution profile is drawn.

Several parameters are used to assess the quality of the labeled protein or peptide. The specific radioactivity of the protein is the amount of radioactivity incorporated per unit mass of protein or peptide. It can be calculated in terms of the total radioactivity employed, the amount of the iodination mixture transferred to the gel filtration column, and the amount of radioactivity present in the labeled protein or peptide, in the damaged components, and in the residual radioiodine. However, in practice, the calculation does not usually take into account damaged and undamaged protein. The specific activity is thus calculated from the yield of the radioiodination procedure, the amount of radioiodide and the amount of protein or peptide used, assuming that there are not significant losses of those two reactants. The yield of the reaction is simply the percentage incorporation of the radionuclide into the protein.

The nature of the materials giving rise to elution peaks from a chromatography column can be checked by employing a specific antiserum to the protein or peptide being radioiodinated. Aliquots (10 μL) of different fractions making up the two peaks are diluted so that each gives the same number of counts (e.g., 5000–10,000 counts/min) per 100 μL). Those samples are incubated with an excess of the antiserum. Only samples containing immunoreactive protein will react with the antiserum. The amount of the radioactive protein associated with the antibody molecules can then be measured by radioimmunoassay.

Having identified the peak or peaks containing the radioiodinated protein or peptide, the yield of the radioiodination can be calculated in terms of the ratio of the total counts associated with the protein or peptide peak to the sum of the total counts associated with the iodide peak.

It is important that the radioiodinated protein or peptide should as far as possible have the same properties as the unlabeled species. Thus the behavior of both molecules can be checked on electrophoresis or ion-exchange chromatography. The ability of the two species to bind to specific antibodies can be assessed by radioimmunoassay.

To store the labelled protein or peptide, immediately after purification, split the sample into small aliquots and then rapidly freeze and store at −20° C. Alternatively, the aliquots can be freeze-dried. Each aliquot should be melted and used only once. Radioiodinated proteins or peptides differ markedly in their stability. Some can be stored for several weeks (though it must be borne in mind that the half-life of $^{125}$I is about 60 d), whereas others can only be kept for several days. If necessary, the labeled protein can be repurified by gel filtration or ion-exchange chromatography prior to use.

The pH optimum for iodination of tyrosine residues of a protein by the chloramine-T method is about pH 7.4. Lower yields of iodinated protein are obtained at pH values below about 6.5 and above about 8.5. Indeed, above pH 8.5, the iodination of histidine residues appears to be favored.

The total volume of the chloramine-T reaction mix should be as low as practically possible to achieve a rapid and efficient incorporation of the radioactive iodine into the protein or peptide. Because of the small volumes of reactants that are employed it is essential to ensure adequate mixing at the outset of the reaction. Inadequate mixing is one of the commonest reasons for a poor yield of radioiodinated protein by this procedure.

If the protein or peptide has been seriously damaged by the use of 50 μg of chloramine-T, it may be worthwhile repeating the radioiodination using much less oxidant (10 μg of less). The minimum amount of chloramine-T that can be used will depend, among other factors, on the nature and amount of protein to be iodinated.

It is normal to carry out the chloramine-T method at room temperature. However, if the protein is especially labile, it may be beneficial to run the procedure at a low temperature.

EXAMPLE 6

Bcr is a Negative Regulator of Bcr-Abl Function

The present example demonstrates reduction of Bcr kinase activity and Bcr/Bcr-Abl complexes by treatment of cells with a 3' BCR anti-sense oligonucleotide.

The facts that p160 BCR is a target for BCR-ABL protein tyrosine kinase and that tyrosine phosphorylated p160 BCR is able to interact within live cells with the Grb2 molecule, an activator of the Ras signaling pathway, are consistent with the hypothesis that p160 BCR plays a role in the pathogenesis of Ph[1]-positive leukemias. Tyrosine phosphorylation of p160 BCR by the activated tyrosine kinase of p145 c-ABL and its subsequent interaction with Grb2 protein indicate that p160 BCR might also be a very important signaling molecule in certain normal physiological processes. In order to address the role of BCR in the oncogenic effects of BCR-ABL, BCR protein expression was specifically eliminated or reduced in cells expressing BCR-ABL. Antisense oligodeoxynucleotides are able to bind to the specific mRNA through base-pairing and then by degradation of the mRNA, interfere with protein expression. Since BCR-ABL lacks 3' BCR coding sequences (amino acid residues 927–1271), a 3' BCR antisense oligodeoxynucleotide should be useful in selectively reducing BCR expression without interfering with BCR-ABL expression.

Figure 13:
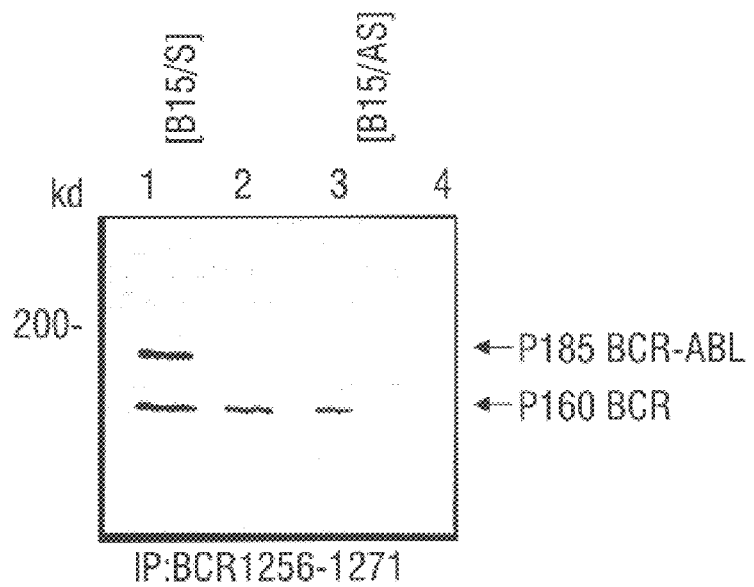
FIG. 13 (Scanned image) shows inhibition of p160 BCR expression by 3' anti-sense BCR oligonucleotide treatment of SUP B15 ALL cells. SUP B15 cells were treated with anti-sense BCR oligonucleotides as in FIG. 12. Equal amounts of cells processed from sense and antisense treated cultures were harvested at day 7. Cells were analyzed for Bcr protein and Bcr/Bcr-Abl complexes by assaying with an antibody to the carboxy terminal of Bcr, as described (Liu et al., 1993). Lane 1 is an SDS gel pattern of the sense treated culture; lane 2 is the assay performed with peptide-blocked antibody. Lane 3 is the pattern from anti-sense treated culture; lane 4 is the peptide-blocked control. Comparison of lanes 1 and 3 indicates that the level of Bcr protein as well as its ability to form Bcr/Bcr-Abl complexes was severely inhibited by 3' BCR anti-sense treatment. Quantitation measurements indicate that the level of Bcr protein was reduced about 10-fold by antisense treatment compared to sense, when normalized for the amount of Abl protein in the cultures.

3' BCR sequences share homology with several human genes such as p21 RasGAP and ABR genes. Therefore, selected 3' BCR sense and antisense oligonucleotide sequences were examined by FASTA search in GeneBank database to eliminate oligonucleotides that share significant homology with known human genes. Examination of the oligonucleotides by a primer selection program showed no significant secondary structure formation. The following oligonucleotide sequences were selected: BCR3351-antisense, 5'ATCATCACCGACACATCC 3', SEQ ID NO:20; BCR3351-sense, 5' GGATGTGTCGGTGATGAT 3', SEQ ID NC:21. The oligonucleotide sequences correspond to BCR coding sequences 3351 to 3368, which are not found within BCR-ABL sequences and other known human gene sequences. The oligonucleotides were synthesized by Genosys Biotechnologies, Inc. (Houston, Tex. 77380-3600). Two phosphotriester linkages were placed at both ends of each oligonucleotide to enhance their resistance to endonuclease digestion and prolong their effects. The effects of the sense and antisense 3' BCR oligonucleotides were tested on BCR expression in SUP-B15 cells, a cell line derived from a Ph[1]-positive acute lymphocytic leukemia patient that expresses p185 BCR-ABL. Immunokinase assays were performed with anti-BCR (1256–1271) peptide antibody (the antibody detects Bcr proteins but not Bcr-Abl proteins) to determine the level of BCR expression in B15 cells after 7 days treatment with either the sense or antisense 3' BCR oligonucleotides (FIG. 13, lanes 1 and 3). The results showed that the antisense treated B15 cells express much lower levels of BCR protein compared with that of the sense treated cells.

Figure 12:
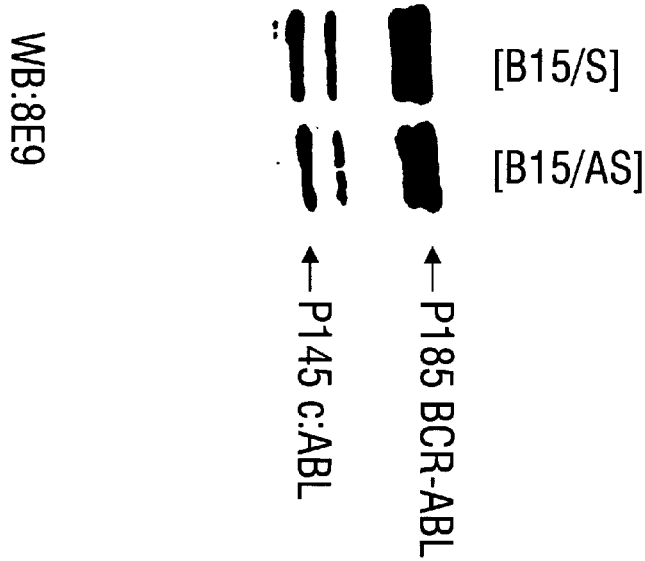
FIG. 12 (Scanned image) shows Bcr-Abl protein expression in SUP-B15 cells treated with sense and anti-sense 3'BCR. SUP-B15 cells express p185 BCR-ABL; they were derived from a patient with Philadelphia chromosome-positive ALL. One-tenth of the cells harvested in the experiment shown in FIG. 13 was assayed for Bcr-Abl expression by Western blotting with the anti-Abl monoclonal antibody 8E9. Quantitation of these results indicates that there was a 35% reduction in Bcr-Abl protein in the anti-sense treated cultures (lane 1) compared to sense (lane 2). Similarly, the Abl protein was reduced about 26% in the anti-sense treated culture compared to sense. Quantitation was done by a densitometer SI unit (Molecular Dynamics).

Since the C-terminal Bcr antibody does not detect Bcr-Abl, the level of co-precipitated Bcr-Abl with Bcr gives an estimate of the amount of Bcr/Bcr-Abl complexes. Of importance, these assays showed that the amount of p160 BCR/p185 BCR-ABL complexes were also reduced in the antisense treated B15 cell compared to the sense treated cells (FIG. 13, lanes 1 and 3). In this study, equal amounts of the sense and the antisense oligonucleotide treated B15 cells were analyzed. Western blot analyses with an anti-Abl monoclonal antibody showed that the expression of p185 BCR-ABL was not significantly altered by the antisense and the sense oligonucleotides treatment (FIG. 12). These results showed the 3' BCR antisense oligonucleotide specifically reduced the expression of normal BCR without interfering with the expression of BCR-ABL.

Quantitation analyses of the p160 BCR observed in lanes 1 and 3 of FIG. 13 by a densitometer (Molecular Dynamics) showed that the antisense treated B15 cells contained about 14 times less Bcr than that of the sense treated cells. However, quantitation analyses of FIG. 12 showed that levels of Bcr-Abl and c-Abl of antisense treated B15 cells were reduced about 1.6 and 1.35 fold, respectively, than that of the sense treated cells. Using c-Abl as an internal control, the actual reduction of p160 BCR in B15 cells by the antisense treatment is about 10 fold.

Figure 20A:
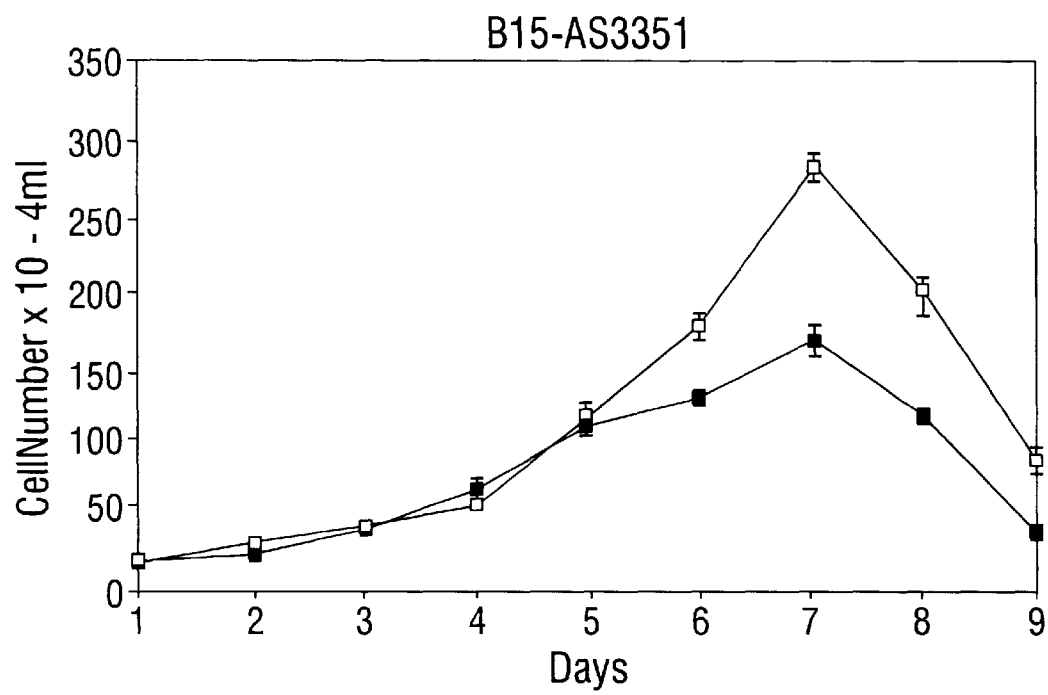
FIG. 20A and 20B show effects of 3' BCR antisense oligonucleotides on the growth of p185 BCR-ABL expressing SUP-B15 cells and p210 BCR-ABL expressing M3.16 cells. (A) B15 cells cultured in 20% FCS containing RPMI media with either the 3' BCR antisense oligonucleotides (10 uM at day 1) (open squares) or the sense oligonucleotides (10 uM at day 1) (closed squares). (B) M3.16 cells cultured in 10% FCS containing DMEM media with either the 3' BCR antisense oligonucleotides (open squares) or the sense oligonucleotide (closed squares) as above. Oligonucleotides were added at day 1 at a final concentration of 10 uM and added again at day 5 at half of the initial concentration. Cell viability was determined by trypan blue dye exclusion. The data are the mean±SEM of a triplicate analysis.
Figure 20B:
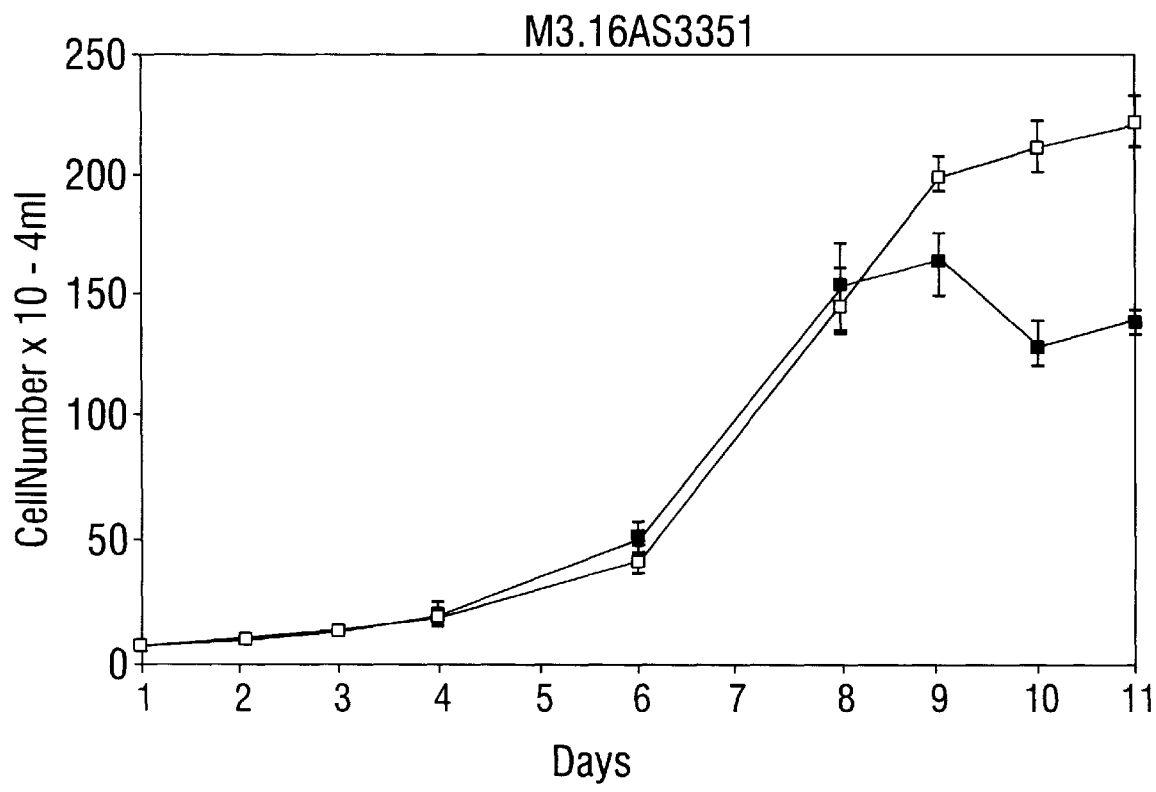

The biological effects of the 3' BCR antisense oligonucleotide treatment were tested on SUP-B15 cells. SUP-B15 cells were seeded in triplicate wells at a concentration of $1.6 \times 10^5$ cells/ml in a 200 μl volume of RPMI media supplemented with 20% FCS. Oligonucleotides were added to the cells at a final concentration of 10 uM. Cell number was monitored by trypan blue exclusion assay for 9 days. The mean cell number of the triplicates was determined each day (FIG. 20A). It was expected that antisense 3' BCR oligo would increase growth of Bcr-Abl expressing cells because of the proven role of Bcr phosphotyrosine 177 in stimulating the Ras pathway (Pendergast et al., 1993; Puil et al., 1994; FIG. 18 and FIG. 19). Results showed that antisense oligonucleotide treatment of SUP-B15 cells sustained a higher growth density compared to sense oligonucleotide treatment. Similar results were obtained from treatment of M3.16 cells (human megakaryocytic cells transfected with p210 BCR-ABL) (FIG. 20B). For this particular experiment, the cell number was followed up for a longer period of time (11 days) and oligonucleotides were added again at day 5 at half of the initial concentration. Light microscopic examination of the cell culture at day 9 revealed that the antisense treated M3.16 cells were more confluent than sense treated cells.

In summary, the present inventor performed experiments to determine whether Bcr protein was reduced by the 3' BCR anti-sense treatment. Therefore, a sufficient amount of p185 BCR-ABL expressing SUP-B15 cells was treated with sense and anti-sense 3' BCR oligos for seven days in culture. Anti-sense treated cultures had twice as many live cells as the sense treated cultures. Two types of assays were performed on these cultures.

First, the level of Bcr-Abl protein was assayed by Western blotting. The anti-sense treated culture had no significant change in the expression of the Bcr-Abl protein compared to the sense-treated culture (FIG. 12). Therefore, the increased rate of growth was not a result of increased Bcr-Abl expression.

Second, lysates of anti-sense and sense-treated cultures were assayed by immune complex kinase assays with antibodies to the carboxy terminus of Bcr, which have been shown to detect Bcr/Bcr-Abl complexes (18, 19). These antibodies detect Bcr directly but not Bcr-Abl protein. However because Bcr can complex with Bcr-Abl, this assay also detects Bcr-Abl which is co-precipitated along with Bcr. Incubation of these immune complexes with labeled ATP causes tyrosine phosphorylation of Bcr by Bcr-Abl and autophosphorylation of Bcr-Abl (19). Comparison of lysates from sense and anti-sense treated cultures showed a dramatic reduction in Bcr and Bcr/Bcr-Abl complexes by anti-sense (FIG. 13). Phosphorimager analyses indicated that the amount of Bcr was reduced about 14-fold by anti-sense 3' BCR. Using Abl Western blot data as an internal control for mass, the specific reduction in Bcr is estimated to be about 10-fold.

Therefore, the data in FIG. 12 and FIG. 13 indicated that the anti-sense 3' BCR oligo dramatically reduced the amount of functional Bcr and Bcr/Bcr-Abl complexes while not significantly affecting the level of Bcr-Abl protein. These results provide support for Bcr being a negative regulator of Bcr-Abl function.

EXAMPLE 7

Normal Bcr Protein has a Negative Regulatory Role

The present example demonstrates that 3' BCR anti-sense treated Bcr-Abl expressing cells maintained in low serum have enhanced survival compared to sense treated cells.

The differences between the growth patterns of sense and antisense oligonucleotide treated cells are not observed until late in the culture cycle. These results suggest that some factor in the medium could overcome the effects of antisense 3' BCR oligonucleotide. It is possible that reduced serum level is required for the effects induced by antisense oligonucleotide treatment.

B15 cells were cultured in a low serum containing media [5% fetal calf serum (FCS)]. These cells normally require 20% FCS. A batch of B15 cells ($2.2 \times 10^6$/ml) was cultured in RPMI containing 5% FCS. 200 μl of this suspension was seeded into each well of a 96 well culture plate. Either the antisense or sense oligonucleotides were added to the culture at a final concentration of 10 μM. The cell numbers were determined as an average of the triplicates and plotted in FIG. 14. B15 cells cultured in low serum containing media were found to have increased survival after treatment with the 3' BCR antisense oligonucleotide compared to sense oligonucleotide treatment. Thus, after five days of treatment with antisense 3' BCR the number of viable cells was about twice that of sense-treated cells. These results indicate that the normal Bcr protein inhibits survival of Bcr-Abl expressing cells under serum conditions that inhibit cell growth. Thus, this result is consistent with normal Bcr protein having a negative effect on cells by stimulating cell death.

Figure 14:
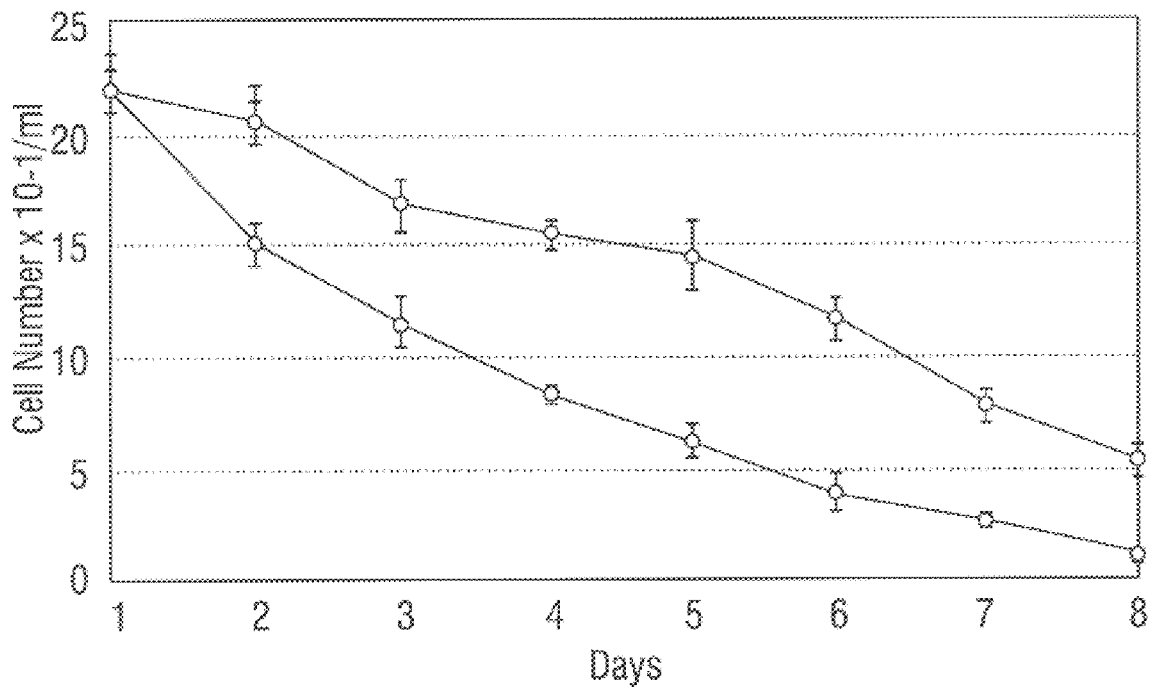
FIG. 14 shows treatment with 3' BCR anti-sense oligo enhances the survival of p185 BCR-ABL expressing SUP-B15 cells maintained in low serum. SUP-B15 cells ($2 \times 10^6$ cells) were maintained in RPMI medium containing 5% fetal calf serum. Cells will not grow under these conditions and will slowly die off since cell growth requires 20% serum. Cells were treated with the 3' BCR anti-sense (open squares) or sense oligo (closed squares) at a concentration of 10 $\mu$M. The number of viable cells was determined by trypan blue dye exclusion. The data are expressed as the mean ($\pm$SEM) of three replicates.

In summary, inspection of the growth rate patterns of sense and anti-sense treated Bcr-Abl expressing cultures showed that the growth stimulatory effects of anti-sense were not seen until a lag of several days. During that lag period, no differences in growth rate between sense and anti-sense treated cells were observed in two cell lines. This lag may be due to optimal growth stimulation provided by high serum concentration in the medium. Therefore, the effects of the anti-sense 3' oligo was tested at decreased levels of serum, under conditions where cells fail to increase in cell number. Anti-sense treated cultures showed enhanced survival when compared to sense (FIG. 14). These results suggest that Bcr protein may stimulate cell death in the presence of Bcr-Abl, and that removal of Bcr will enhance survival of Bcr-Abl expressing cells.

EXAMPLE 8

Phosphorylation of Bcr inhibits its Ser/Thr Kinase Activity and Blocks the Negative Regulatory Role of Bcr The present Example demonstrates inhibition of Ser-Thr Bcr autophosphorylation activity by Bcr-Abl. Normal Bcr protein, in addition to enhancing the growth stimulatory effects of Bcr-Abl, also has a negative regulatory role as shown in Example 6. The present results indicate that normal Bcr counteracts the growth effects of Bcr-Abl and that this negative effect of Bcr is neutralized by tyrosine phosphorylation of Bcr by Bcr-Abl. Bcr-Abl and Bcr appear to be in an intracellular battle. Bcr-Abl is stimulating malignant growth whereas non-tyrosine phosphorylated Bcr is inhibiting growth. Moreover, Bcr-Abl can inhibit the kinase activity of Bcr by tyrosine phosphorylation. The Ser/Thr kinase function of Bcr is presumed to be responsible for its negative growth effects. Therefore, since tyrosine phosphorylation of Bcr will inhibit its Ser/Thr kinase activity, blocking the Ser/Thr kinase function of Bcr will block its negative growth function.

Figure 15:
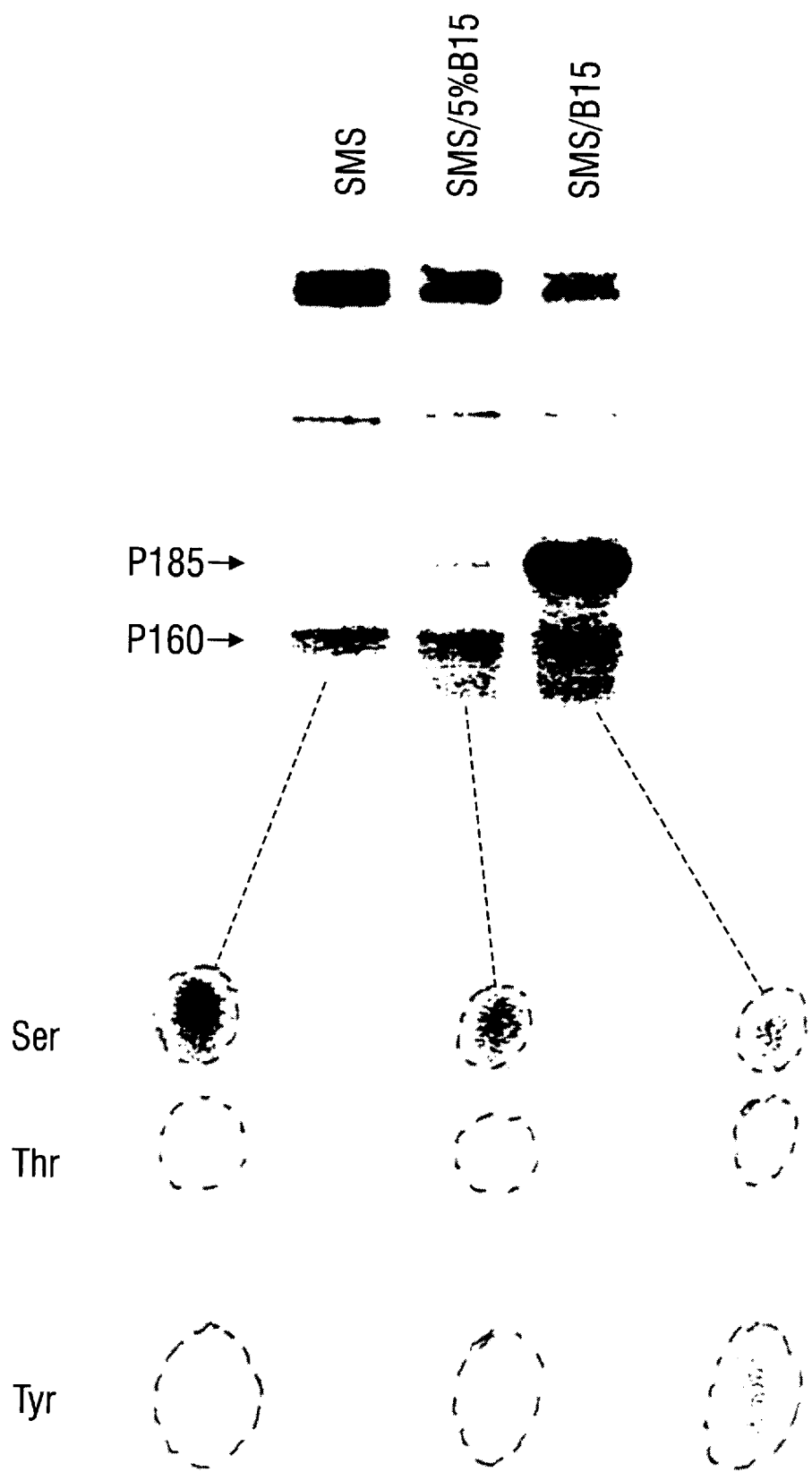
FIG. 15 (Scanned image) shows depression of Bcr serine/threonine autokinase activity by the Bcr-Abl tyrosine kinase. (In vitro transphosphorylation of Bcr by Bcr-Abl). Equal amounts of cell extract from $3 \times 10^8$ SMS-SB cells (lacking Bcr-Abl) were divided into three portions and processed for immunoprecipitation with anti-Bcr (1256–1271). One portion (from $1 \times 10^8$ cells) was collected on protein A Sepharose beads for the immunokinase assay. The second portion ($1 \times 10^8$ cells) was added to anti-Abl(51–64) immune complexes bound to protein A Sepharose beads obtained from $1 \times 10^6$ SUP-B15 (p185 BCR-ABL expressing cells). These anti-Abl immune complexes have a high amount of p185 BCR-ABL but only a trace level of p160 BCR. The third batch of Bcr immune complexes ($1 \times 10^8$) were added to Bcr-Abl immune complexes obtained from $2 \times 10^7$ SUP-B15 cells. The whole procedure was performed as described (Liu et al., 1993). Phosphoamino acid analysis of gel purified p160 BCR following transphosphorylation by low and high levels of Bcr-Abl. The three p160 BCR bands from panel A were eluted from the gel by SDS buffer and treated with 6 N HCl for 90 min at 110° C. These conditions are a reasonable compromise to obtain both phospho serine/threonine and tyrosine values. The hydrolysate was fractionated on a thin layer plate under conditions for separating phospho serine/threonine and tyrosine (Liu et al., 1993). About 200 cpm (Cerenkov) of acid hydrolysate from the p160 SMS-SB band, 200 cpm of the SMS-SB/5% SUP-B15 p160 band, and 500 cpm of the SMS-SB/100% SUP-B15 p160 band were loaded on the plate. After normalization, the intensities of the serine/threonine spots were 4,421 for p160 Bcr alone; 1763 for p160 BCR incubated with a low level of Bcr-Abl (5%), and 142 for p160 BCR incubated with the high level of Bcr-Abl. Phospho serine/threonine was reduced more than 30-fold by Bcr-Abl kinase at relatively high levels and by 2.5-fold at the 5% Bcr-Abl level.

Bcr-Abl catalyzed in vitro phosphorylation of Bcr (harvested from cells lacking Bcr-Abl) reduces the level of Bcr autophosphorylation. Therefore, the following study was carried out. The phosphoamino acid ratios of gel purified Bcr labeled in the immunokinase assay with [$^{32}$P] ATP with no added Bcr-Abl immune complexes was compared to that labeled with a relatively high level of Bcr-Abl immune complexes, and to that with addition of a low amount of Bcr-Abl (5% of the high level). Addition of Bcr-Abl immune complexes to Bcr immune complexes in kinase assays showed phosphorylation of Bcr-Abl and Bcr (FIG. 15). The level of phosphorylated Bcr-Abl increased with increased levels of Bcr-Abl immune complexes, but the intensity of the phosphorylated Bcr band did not change appreciably. However, phosphoamino acid analyses of the Bcr band under these different conditions showed a dramatic decrease in the phosphoserine/threonine content of the Bcr band with a relatively low level of Bcr-Abl complexes (FIG. 15). Quantitative analyses indicated that serine/threonine autophosphorylation of Bcr was reduced more than 2.5-fold by a low level of Bcr-Abl (5%). With a high level of Bcr-Abl complexes, the level of Bcr autophosphorylation was reduced about 30-fold. These results indicate that the level of tyrosine phosphorylation of Bcr may be directly correlated with the level of inhibition of Bcr autophosphorylation activity.

Figure 16:
FIG. 16 (Scanned image) shows transphosphorylation of casein by Bcr and Bcr/Abl. T-150 flasks of COS 1 cells were transfected with either pSG5 BCR or pSG5 BCR-ABL. Two days after transfection, cells were harvested and the kinase performed as in Liu et al., 1993. In lane 3, the same amount of protein A Sepharose beads with Bcr complexes as in lane 2 was added to protein Sepharose beads with Bcr-Abl complexes harvested with anti-Abl (51–64) p6D monoclonal antibody. Casein (10 $\mu$g) was added to each reaction mixture along with the labeled ATP. After 15 min on ice, the reaction was stopped and the sample treated with hot SDS sample buffer. After removal of the protein A Sepharose beads, the supernatant fluid was fractionated on a 8% SDS gel. Lane 1, p160 BCR autophosphorylation in the absence of casein; lane 2, transphosphorylation of added casein by Bcr, lane 3, transphosphorylation of casein by a mixture of p160 BCR and p210 BCR-ABL.
Figure 17:
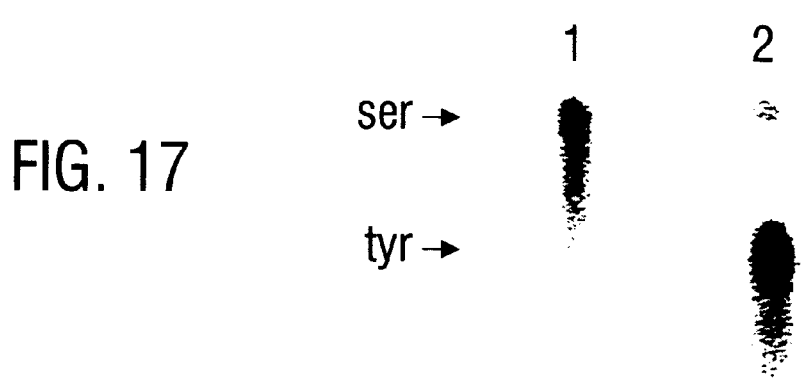
FIG. 17 (Scanned image) shows phosphoamino acid analysis of casein phosphorylated by Bcr and Bcr/Bcr-Abl. Approximately equal cpm of casein from each of the reaction mixtures in Panel A was treated with 6N HCl for 90 min to favor detection of both phosphoserine/threonine and phosphotyrosine. Casein phosphorylated by Bcr (from lane 2 of panel A) is shown in lane 1; lane 2 shows the analysis of casein phosphorylated by the Bcr/Bcr-ABl mixture (from lane 3 of panel A). Despite the presence of equal amounts added Bcr kinase in lanes 2 and 3 of panel A, serine phosphorylation of casein by Bcr was severely inhibited by added Bcr-Abl. That Bcr-Abl was present and active is shown by the strong signal of phosphotyrosine in the added casein molecules in the presence of Bcr-Abl.

Studies were performed to determine whether the transphosphorylation function of Bcr was similarly inhibited by Bcr-Abl catalyzed tyrosine phosphorylation (FIG. 16 and FIG. 17). In these studies, casein (10 µg) was added to the kinase reaction mixtures to allow transphosphorylation of the added substrate by Bcr or by Bcr mixed in vitro with Bcr-Abl (FIG. 16 and FIG. 17). The results showed that transphosphorylation of casein by Bcr was quite effective (FIG. 16, compare lanes 1 and 2). Moreover, phosphoamino analysis established that casein was phosphorylated on serine and threonine residues (FIG. 17, lane 1). Of interest, although the phosphorylation of added casein was stimulated when Bcr-Abl was added to Bcr (FIG. 16, lane 3), the level of casein serine/threonine phosphorylation was greatly inhibited while at the same time casein was strongly phosphorylated on tyrosine residues (FIG. 17, lane 2). These results show quite clearly that the Bcr-Abl oncoprotein inhibits the transphosphorylation function of normal Bcr.

These results support the hypothesis that Bcr-Abl may in fact be able to neutralize the negative effects of Bcr by tyrosine phosphorylation of first exon sequences within Bcr. It is the first exon of Bcr that functions as a Ser/Thr protein kinase. Several tyrosines within or near the kinase domain of Bcr are phosphorylated by Bcr-Abl. The kinase domain of Bcr would include residues 163–355 (20, 21); the present disclosure demonstrates that tyrosines at positions 177, 283 and 360 are phosphorylated within the normal Bcr protein as a result of Bcr-Abl catalyzed phosphorylation. Several other first exon tyrosines are likely to be phosphorylated also. One or more of these tyrosine phosphorylations might change the shape of the Bcr protein in a way that inhibits its serine/threonine kinase activity.

Therefore, a vector that introduces excessive amounts of normal Bcr into bone marrow cells of the leukemia patient is provided by the present invention. It should function just as the Bcr-159 fragment (Examples 7 and 9) to inhibit the Bcr-Abl kinase and, more importantly, the functional effects of Bcr should neutralize the malignant form of Bcr-Abl directly. Normal BCR would be inserted into a retrovirus vector; this vector would be transfected into a packaging cell line that generates an amphotropic host range defective virus. This virus would be used to infect stem cells from the bone marrow of autotransplant patients (see Example 9). The normal Bcr protein has 1271 amino acids and the sequence is presented in M. L. Campbell and R. B. Arlinghaus, "Current Status of Bcr Gene Involvement with Human Leukemia", Advances in Cancer Research, 57:227–255, 1991, which is incorporated by reference herein.

EXAMPLE 9

Expression of Bcr Fragments

N-terminal Bcr fragments have been expressed in monkey cells. Materials and methods used in this example include the following: COS1 cells ATCC #CRL 1650 (Rockville, Md.) COS1 is a fibroblast-like cell line established from simian kidney cells (CV1) that were transformed by an origin-defective mutant of SV40, that codes for wild-type T antigen. COS1 cells were cultured at 37° C. with 5% $CO_2$ in DMEM (Grand Island Biological Co. (Gibco) Grand Island, N.Y.) supplemented with 10% fetal calf serum (Gibco Laboratories, Grand Island, N.Y.). Transient transfections of COS1 cells were performed by the diethylaminoethyl (DEAE)-Dextran procedure. Transfection was initiated when COS1 cells were about 60%–80% confluent. After washing once with phosphate-buffered saline (PBS) and once with Tris-buffered Saline-0.02% Dextrose (TBS-D), cells were incubated with TBS-D containing 0.2 mg/ml DEAE-Dextran and 2 µg/ml of each added plasmid. The supernatant was then removed after 5–10 minutes when the cells started to round up and shrink. After washing once with TBS-D and once with PBS, the cells were incubated in DMEM supplemented with 10% fetal calf serum and 100 µg/ml of chloroquine at 37° C. The chloroquine containing media was removed after 3–5 hours and the cells were washed three times with DMEM without fetal calf serum. The cells were then incubated in DMEM supplemented with 10% fetal calf serum at 37° C. for 2–3 days before harvesting.

Figure 6A:
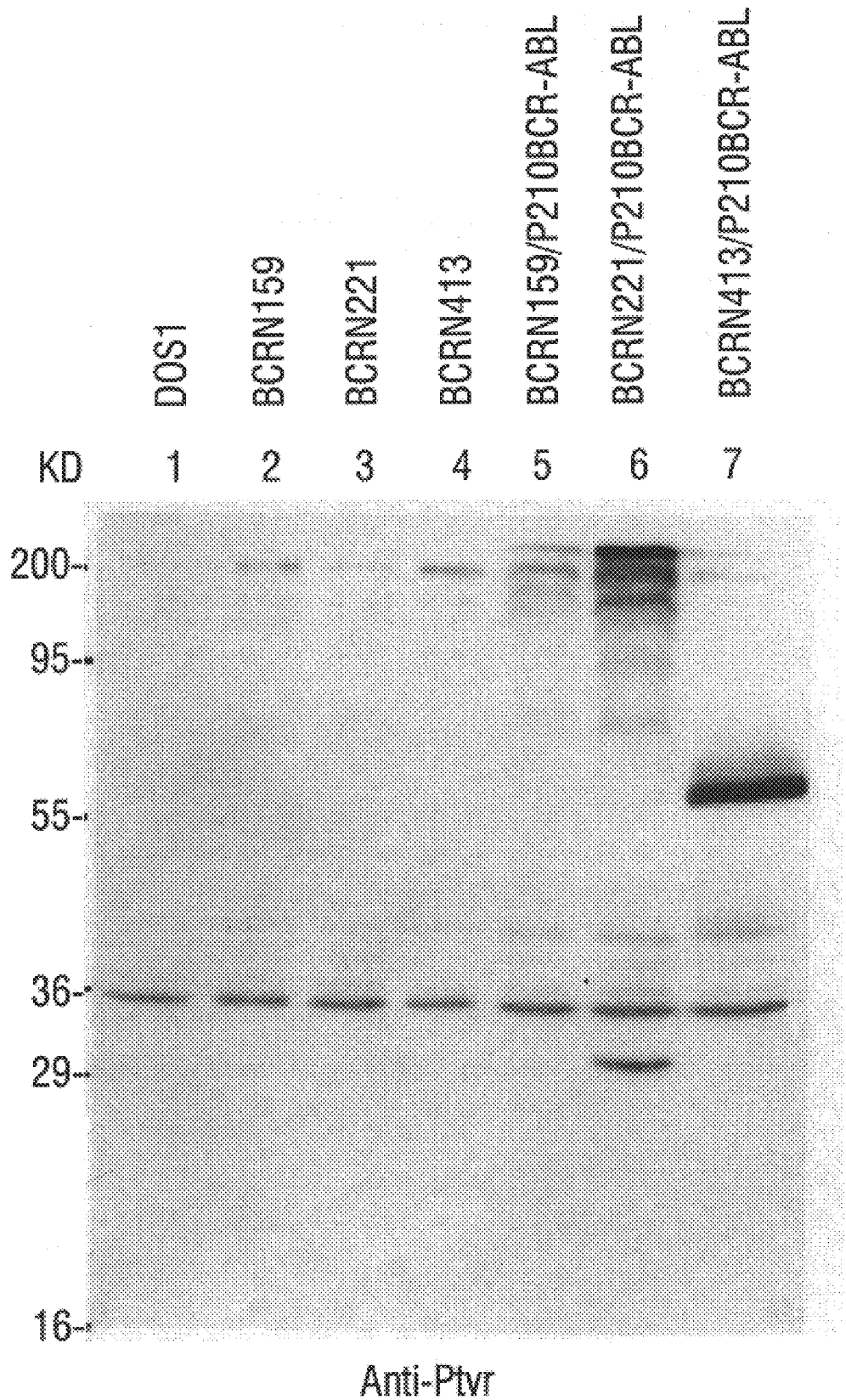
FIG. 6A and FIG. 6B. (Scanned images) In vivo tyrosine phosphorylation of truncated Bcr first exon sequences by Bcr-Abl. COS-1 vectors expressing Bcr150, Bcr221, and Bcr413 proteins, respectively, were expressed in COS-1 cells in the presence and absence of p20 Bcr-Abl.
Figure 6B:
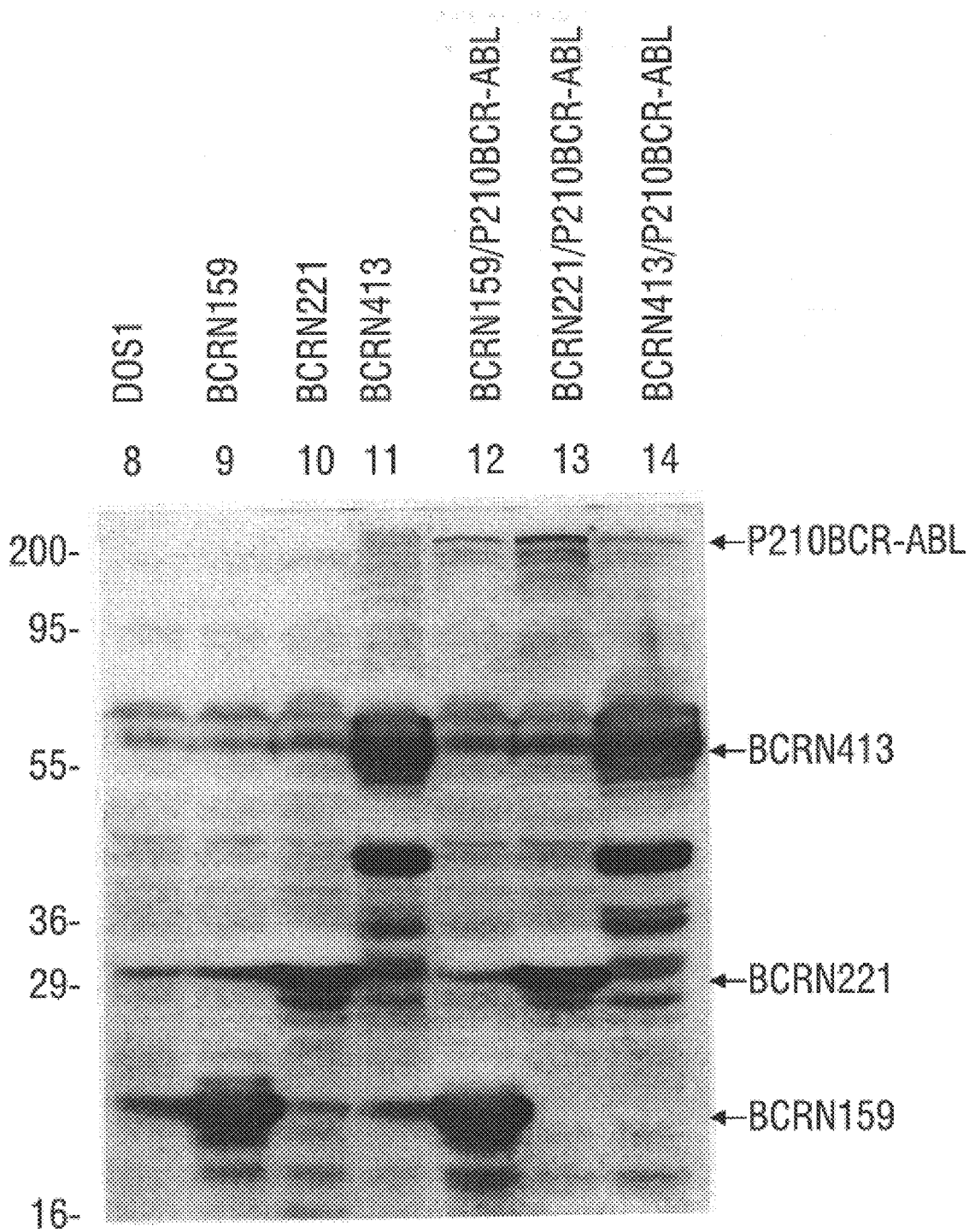

COS-1 vectors expressing Bcr159, Bcr221, and Bcr413 proteins, respectively, were expressed in COS-1 cells in the presence and absence of p210 Bcr-Abl. FIG. 6A shows a Western blot with Anti-pTyr antibody. Bcr-Abl induces tyrosine phosphorylation of Bcr221 and Bcr413 but not Bcr159, indicating that the first two tyrosines of Bcr are not targets for Bcr-Abl. The next tyrosine is at residue 177, and it is expected to be phosphorylated by Bcr-Abl[3]. Bcr221 is tyrosine phosphorylated, but as with Bcr413, only in the presence of Bcr-Abl. FIG. 6B shows a Western Blot of the same extracts probed with anti-Bcr 1–16. Note that all three Bcr proteins fragments are specifically expressed under both conditions. In summary, Bcr159 is not phosphorylated in cells expressing Bcr-Abl despite the presence of two tyrosines (FIG. 6A and FIG. 6B). In contrast, a 221 residue N-terminal fragment and a 413 N-terminal fragment of Bcr are expressed and both are phosphorylated on tyrosine 177 in cells expressing Bcr-Abl.

EXAMPLE 10

Liposome-encapsulated Peptides

The present example outlines a method that may be used to associate the peptides of the present invention with liposomes. These liposome preparations will then be used to determine their effects on Bcr-Abl kinase activity and adapter protein binding to Bcr-Abl in cell lines from patients and other cells expressing active Bcr-Abl.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Liposomes bear many resemblances to cellular membranes and are contemplated for use in connection with the present invention as carriers for the BCR peptides. They are widely suitable as both water- and lipid-soluble substances and can be entrapped, i.e., in the aqueous spaces and within the bilayer itself, respectively. It is possible that drug-bearing liposomes may even be employed for site-specific delivery of active agents by selectively modifying the liposomal formulation.

The formation and use of liposomes is generally known to those of skill in the art. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins such as cytochrome c bind, deform and penetrate the bilayer, thereby causing changes in permeability. Cholesterol inhibits this penetration of proteins, apparently by packing the phospholipids more tightly.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical property of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity and surface charge. They may persist in tissues for hours or days, depending on their composition, and half lives in the blood range from minutes to several hours. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

EXAMPLE 11

Delivery of BCR-ABL Peptides via Adenovirus or a Retrovirus

This prophetic example describes some of the ways in which the present invention may be of use in the treatment of leukemia where Philadelphia positive cells are present. Nucleic acid sequences encoding BCR peptides or fusion proteins may be introduced into bone marrow to provide a copy of a BCR synthetic gene and therefore, also a protein product comprising BCR peptides or fusion peptides that would bind to adapter proteins and inhibit the ras oncogene pathway, and bind to the coiled coil area of BCR-ABL to inhibit autophosphorylation.

Retrovirus transduction of the various Bcr peptide motifs described in Examples 1 and 2 is to be performed to identify their inactivation of Bcr-Abl or interference with the leukemic activity of Bcr-Abl.

Figure 11:
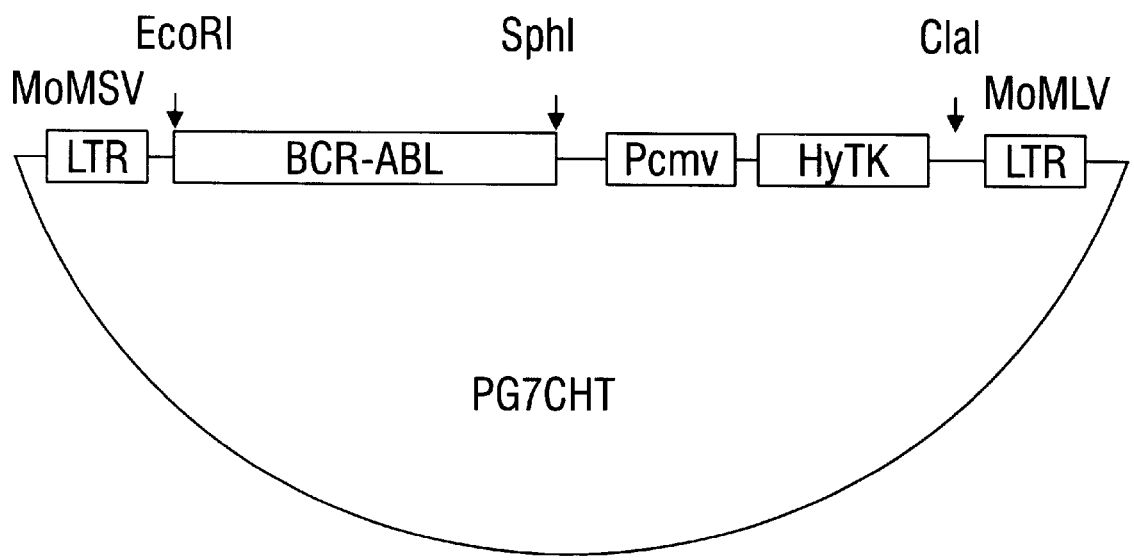
FIG. 11 depicts a retroviral vector pG7CHT useful for introducing peptides of the present invention into cells.

A retroviral vector pG7CHT (FIG. 11) containing the BCR-ABL gene was obtained from Dr. Albert Deisseroth. The pA317 amphotropic retrovirus packaging cell line (American Type Culture Collection, Rockville, Md., #CRL9078) will be used for producing high titer virus. The BCR-ABL gene will be released from the plasmid by digesting with EcoRI and SphI restriction endonucleases. A full length BCR gene released from pSG5BCR plasmid by digesting with EcoRI and SphI restriction enzymes will then be inserted into the EcoRI and SphI sites of pG7CHT vector. The BCR gene will be expressed under MoMSV/LTR. The vector also contains a hyromycin resistant gene (HyTK) which is expressed under a CMV promotor (Pcmv). The N-terminal fragments of BCR will be expressed using the same strategies described above.

The Bcr 421 fragment should interfere with Bcr-Abl oligomerization, and contain all the phosphorylation sites of native Bcr-Abl. Therefore, overexpression of this fragment should have all the inhibitory activities of the first exon of Bcr. However, it would not directly interfere with Shc and Crkl effects but because it should inhibit oligomerization of Bcr-Abl, the kinase activity of Bcr-Abl should be greatly reduced. Therefore, Crkl and Shc should not be tyrosine phosphorylated to any great extent.

Note that full length BCR with stop codons in all three reading frames at codon 422 was inserted into the vector. Therefore, only the 421 fragment is made. Similarly, the Bcr159 fragment and the Bcr 221 fragment were made by inserting stop codons after codon 159 and 221, respectively.

Human adenoviruses are a further means for introducing nucleic acid expression vectors into tissue. Adenoviruses are double-stranded DNA tumor viruses with genome sizes of approximately 36 kb. As a model system for eukaryotic gene expression, adenoviruses have been widely studied and well characterized, which makes them an attractive system for development of adenovirus as a gene transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

In general, adenovirus gene transfer systems are based upon recombinant, engineered adenovirus which is rendered replication-incompetent by deletion of a portion of its genome, such as E1, and yet still retains its competency for infection. Relatively large foreign proteins can be expressed when additional deletions are made in the adenovirus genome. For example, adenoviruses deleted in both E1 and E3 regions are capable of carrying up to 10 kb of foreign DNA and can be grown to high titers. Persistent expression of transgenes follows adenoviral infection.

Particular advantages of an adenovirus system for delivering foreign genes and their protein products to a cell include (i) the ability to substitute relatively large pieces of viral DNA with foreign DNA; (ii) the structural stability of recombinant adenoviruses; (iii) the safety of adenoviral administration to humans; (iv) lack of any known association of adenoviral infection with cancer or malignancies; (v) the ability to obtain high titers of the recombinant virus; and (vi) the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible.

Human subjects testing positive for the Philadelphia chromosome and for whom the medical indication for adenovirus-mediated gene transfer has been established would be tested for the presence of antibodies directed against adenovirus. If antibodies are present and the patient has a history of allergy to either pharmacological or naturally occurring substances, application of a test dose of on the order of $10^3$ to $10^6$ recombinant adenovirus under close clinical observation would be indicated.

Recombinant adenovirus providing BCR peptides or fusion peptides of the present invention is prepared and purified by any method that would be acceptable to the Food and Drug Administration for administration to human subjects, including, but not limited to cesium chloride density gradient centrifugation, and subsequently tested for efficacy and purity. Virus is administered to patients by means of administration to bone marrow in any pharmacologically acceptable solution, either as a bolus or as an infusion over a period of time. Generally speaking, it is believed that the effective number of functional virus particles to be administered would range from $5\times10^{10}$ to $5\times10^{12}$.

Patients would remain hospitalized for at least 48 hr to monitor acute and delayed adverse reactions. Bone marrow levels of Philadelphia chromosome-positive cells may be monitored. Adjustments to the treatment may include adenovirus constructs that use different promoters or a change in the number of pfu administered.

EXAMPLE 12

Proposed Method of Treating a Bone Marrow Sample with Bcr-Abl Peptides to Selectively Inhibit Philadelphia Chromosome-Positive Cells The present example is provided to outline a preferred embodiment of a proposed method whereby an autologous bone marrow sample may be obtained and processed ("pretreated") so as to purge the bone marrow of leukemic (Philadelphia chromosome-positive) cells in vitro prior to in vivo injection. The in vitro method proposed herein may also advantageously enrich the bone marrow population of diploid (normal) cells, thus enhancing the therapeutic capacity in the leukemic patient to whom it is administered.

As used in the present example, a "normal cell" is a cell in bone marrow which is Philadelphia chromosome-negative. A "normal cell" is also defined as a bone marrow cell which is dependent upon ABL within the cell for growth.

Accordingly, a bone marrow sample of at least 1000 ml. containing $2\times10^{10}$ or $2\times10^8$/kg of nucleated cells is collected under sterile conditions from a leukemic patient. The sample is then to be subjected to Ficoll hypaque or Percoll discontinuous gradient separation. The nucleated cells (immature) are collected from the interface. This reduces the number of nucleated cells 5-fold (to $4\times10^7$/kg). The cells are then subjected to antibody separation by removing DR (Class II HLA antigen family expressed in dividing hematopoietic cells) positive cells by immunoadherance separation. This reduces the number of cells to $2-5\times10^7$ cells. These remaining cells are then resuspended at $5\times10^5$ cells per cc of tissue culture medium (40–100 cc) of HL1 medium, supplemented with 1000 U of GMCSF and IL3, and incubated with BCR peptides for 3 days.

The Bcr-Abl peptides (or phosphopeptides) packaged in liposomes are then to be added to a cell culture of bone marrow cells and cell supportive culture medium at a concentration of between 1 and 100 $\mu$M. Most preferably, the BCR peptides have a sequence composition comprising a Bcr-Abl peptide or peptides capable of inhibiting Bcr-Abl induced activation of Ras, said peptide or peptides having a Bcr-Abl amino acid sequence that includes tyrosine 177, 283, and 360. The BCR peptides, most preferably, are to be added to the bone marrow cell culture system at a concentration of 10 $\mu$M. After approximately 3 days in culture, changing the medium daily, the culture is to be examined to determine the ratio of leukemic cells to normal cells.

A ratio of not more than 1 leukemic cell:100 normal cells is considered acceptable for use as a therapeutic bone marrow transplant for a leukemic patient. This ratio was chosen as clinical studies have shown that reduction of the ratio of normal cells to leukemia cells significantly below 100 to 1 respectively, leads to prolonged remissions post transplant.

"Purged", Philadelphia chromosome-positive cell-depleted, diploid cell-"enriched" (Philadelphia chromosome-negative cell) autologous bone marrow samples, as processed above, may then be reintroduced into the transplant recipient patient according to the procedure outlined in Example 11.

EXAMPLE 13

Method of Treating Leukemia In Humans with BCR Peptide-Treated Tissue Transplants The present example is provided to demonstrate a method by which the described BCR peptide therapy may be used as part of an overall therapeutic regimen, or alone, for treating leukemia. Specifically, the inventors contemplate the use of the described BCR peptide therapy methods for the processing and purging of bone marrow samples that contain Philadelphia chromosome-positive cells. According to one embodiment, the treated tissue is enriched for Philadelphia chromosome-negative cells, and may be reintroduced into the leukemic animal as an autologous transplant. As such, a therapeutic tool to treat a patient with leukemia is provided.

As part of a total clinical treatment protocol for a patient, the method is hypothesized to provide at least a two-log (100-fold) reduction in the ratio of leukemic cells to normal cells, in addition to the 10,000/1 to 1/1 reduction (from chemotherapy) and the 2-log reduction (from fractionation of the marrow cells subsequent thereto) of leukemia cells to normal cells which may be achieved with conventional treatment regimens with non-pre-treated bone marrow tissue transplants. The proposed regimen thereby effectively reduces the number of leukemia cells in the patient to levels which enhance the therapeutic index of the bone-marrow transplant treatment. In some cases, an up to 3-log reduction (1000-fold) in the number of Philadelphia chromosome-positive cells in a patient's bone marrow cell population is achievable upon the reintroduction of a pretreated bone marrow sample.

The reintroduction of a patient's pre-treated autologous bone marrow sample also offers a method for curing CML disease and for preventing the transition of leukemia from its chronic phase to the more serious forms of acute leukemia. A processed autologous bone marrow sample according to the claimed methods depletes the Philadelphia chromosome-positive population of marrow cells while enriching the population of normal hematopoietic progenitor cells (diploid cells) of the tissue sample.

A processed autologous bone marrow sample according to the claimed method is used as part of a total leukemia treatment regimen. Once a prepared bone marrow sample is processed according to the methods disclosed herein, standard protocols employed for the general technique of performing a bone marrow transplant in CML may be used to obtain an initial bone marrow sample and to reintroduce the processed bone marrow to the patient. Such general clinical techniques are described by Canaani et al.[13], which reference is specifically incorporated herein by reference for this purpose. A volume of about 50–100 cc of purified marrow (containing about $2.5 \times 10^7$ cells) is the volume of processed bone marrow tissue which will be given to the patient to effect the claimed treatment.

A proposed method for treating leukemia in a patient according to the present invention comprises: identifying a patient having leukemia; administering to the identified patient a chemotherapeutic regimen sufficient to generate cytogenetic remission in the patient in the ratio of leukemia cells to normal cells; obtaining a bone marrow sample from the identified patient in cytogenetic remission; exposing the bone marrow sample from the patient in cytogenetic remission to a Philadelphia chromosome-positive cell cytotoxic concentration of BCR peptides to provide an essentially Philadelphia chromosome-positive cell free bone marrow sample; and reintroducing the essentially Philadelphia chromosome-positive cell free bone marrow sample into the identified patient, wherein the reintroduction of the essentially Philadelphia chromosome-positive cell-free bone marrow sample provides replacement of Philadelphia chromosome-positive marrow cells with normal hematopoietic progenitor cells in a method for treating leukemia.

In a most preferred embodiment, the bone marrow sample is exposed to about 10 $\mu$M of each BCR peptide (or phosphopeptide) having a composition comprising a Bcr-Abl peptide or peptides capable of inhibiting Bcr-Abl induced activation of Ras, said peptide or peptides having a Bcr-Abl amino acid sequence that includes tyrosine 177, 283, and 360 in a serum-free culture media system. As part of the BCR-peptide pre-treatment of a patient bone marrow sample, any normal (Philadelphia chromosome-negative) cells present in the patient sample are allowed to proliferate so as to "enrich" their concentration in the culture prior to reintroduction of the BCR peptide-treated bone marrow sample to the patient.

Preferred Patient Profile Eligibility

The following presents a generalized patient profile defining those characteristics most desirable in a prospective BCR-peptide-therapy patient.

1. Interferon refractory CML patients in initial chronic phase, or second chronic phase after accelerated phase or blast crisis are particularly well suited for therapy according to the presently described invention. Patients who have bone marrow collected and stored in the chronic phase, or who have been reinduced into chronic phase, are particularly preferred as treatment subjects for the proposed therapy.

2. Patients most preferably should be off interferon therapy for about four weeks prior to storage of an autologous bone marrow sample to be pre-treated with BCR-peptides. However, prior treatment with interferon does not disqualify a patient from eligibility for the proposed BCR-peptide therapy where such a regimen had been discontinued at least four weeks prior to bone marrow sampling.

3. Patients must have a performance of <3 on the Zubrod scale (see Table 3—Zubrod Scale), a creatinine level less than 1.6 mg %, acceptable cardiac condition (class I or II), normal liver functions with bilirubin less than 2 mg %, and an acceptable pulmonary condition (FEV and DLCO >50% of predicted). Patients should be free of infections at the time of treatment.

TABLE 3

| Zubrod Scale | |
| --- | --- |
| Performance Status | Activity |
| 0 | No signs or symptoms |
| 1 | Minor signs or symptoms |

TABLE 3-continued

Zubrod Scale

| Performance Status | Activity |
|---|---|
| 2 | Ambulatory > 50% of time |
| 3 | Ambulatory < 50% of time |
| 4 | Bedridden |

4. A serum creatinine less than 1.6 and SGOT within the normal range is requires.

Treatment Plan

1. Bone marrow aspiration and collection of peripheral blood stem cells and storage: Bone marrow is to be aspirated according to standard techniques and stored when the patient is in an initial chronic phase or after reinduction into chronic phase by chemotherapy. In vivo (chemotherapy) methods will be used to reduce the level of Philadelphia chromosome-positive cells in the population of transplanted cells, following which the marrow will be collected and treated with BCR-peptides.

2. The procedure for BCR-peptide treatment is as follows:
   a. The nucleated cells of the bone marrow sample (approximately $1.4 \times 10^{10}$ nucleated cells for a 70 kg weight human patient) will be concentrated on a ficoll hypaque gradient to remove cells of limited proliferative capability (this reduces the total number of cells by 5-fold). The remaining (approximately $2.8 \times 10^9$) cells will then be further treated with SEPHAROSE® beads conjugated with antibodies to DR antigens. Preparations of marrow thus treated have been observed to generate rapid hematopoietic recovery using the inventor's methods. This will reduce the total number of cells by 10-fold ($2.8 \times 10^8$). The cells will then be diluted in 50 cc of HL1 medium supplemented with 1,000 units of GMCSF and IL-3 (concentration of cells is $5.6 \times 10^6$/cc).
   b. The cells will be incubated for three days in sterile medium at 37° C. in the presence of 10 mM of each BCR-peptide as liposomes.
   c. Following rinsing, the BCR-peptides will be washed from the cells. The cells will then be cryopreserved by standard procedures practiced in the inventors' laboratory.

If this or other in vitro techniques are not available for removing Philadelphia chromosome-positive cells, a combination of peripheral blood and marrow may be utilized which has been collected in chronic phase, or which has been collected following reinduction of chronic phase in the patient with chemotherapy. Multiple bone marrow aspirations from the patient's iliac crests will be performed before the administration of such agents as cytoxan, VP-16 and TBI. A second bone marrow storage will be considered if less than $4 \times 10^8$ total nucleated cells/kg are collected, $2 \times 10^8$ cells/kg of which will be used for the BCR peptide incubation and $2 \times 10^8$ cells/kg of which will be used as a back-up.

Another criterion for adequacy of the amount of nucleated cells of a marrow sample collected from a patient will be $4 \times 10^4$ CFUGM/kg.

Alternatively, cells from the peripheral blood may be collected for reconstitution as a back-up. A dose of $6 \times 10^8$ mononuclear cells/kg from the peripheral blood or $2 \times 10^4$/kg CFUGM is required as a back-up.

Treatment Plan

The preparative marrow ablative regimen will consist of the following systemic chemotherapy:

Cyclophosphamide: 60 mg/kg in 0.5 liter D5W intravenously over 3 hours daily for 2 days—days 1 to 2 (total 120 mg/kg).

VP-16: 125 mg/m² in 1 liter of normal saline is to be administered intravenously over 3 hours every 12 hours daily×3 (6 doses on days 1–3) (total 750 mg/m²).

The hydration given along with the VP16 and cyclophosphamide is 4 liters every 24 hours, as tolerated. This will be supplemented as necessary to maintain intravascular fluid volume and urine output of the patient.

Total body irradiation: Total body irradiation is about 1020 centrigrays. The patients are placed in the supine position and the TBI is directed from the right side with a calculated mid plane dose of 170 rads/fraction, each fraction even bid starting on day 6–8. Autologous bone marrow will then be reinfused on day 9 after the last dose of TBI, after premedication with benadryl 25 mg and solucortef 100 mg 30 minutes before reinfusion to prevent anaphylactic reactions.

Treatment in a 12LP (Protected Environment) is most preferred. Patients will most preferably remain there until the attainment of 500 granulocytes/mm³. Patients will receive bactrim DS po BID and ketoconazole 200 mg poq8h while hospitalized. All blood products will be irradiated from the start of treatment and for three months following transplantation.

Maintenance Therapy: Interferon maintenance therapy will begin 6 weeks after engraftment (a return of the platelet count to greater than 0000/deciliter and an absolute granulocyte count greater than 2,000/deciliter); at a dose of 3 to $9 \times 10^6$ units, the dose to be adjusted to keep to WBC counts between 2 and $4 \times 10^3/\mu l$ with a platelet count >$50 \times 10^3/\mu l$.

Pre-Treatment Evaluation

Bone marrow aspirate and biopsy for morphology, pathology and cytogenetics will most preferably be obtained prior to treatment. An EKG and CXR will be performed on all patients. A urinalysis will also be obtained before therapy. Pulmonary function studies with diffusion capacity, where permitted, will also be conducted.

Evaluation During Study

CBC, platelet, and differential measurements will be obtained every 1–2 days during the initial induction.

Bone marrow aspirate and biopsy for morphologic pathology should be performed at marrow recovery (when WBC count >1.5 K/$\mu l$).

Upon marrow recovery, a full work-up including CBC, platelet count and differential, SMA 12, and marrow studies including cytogenetics will be performed. Studies at remission will include CBC, platelet count, differential and SMA 12 every 1–4 weeks, marrow studies with cytogenetics every 1–3 months and as indicated by disease status.

Criteria for Response and Toxicity

Criteria for response will be similar for all phases of disease as follows:

Complete hematologic remission—normalization for at least 4 weeks of the bone marrow (less than 5% blasts) and peripheral blood with WBC<$10 \times 10^3/\mu l$ and no peripheral blasts, promyelocytes or myelocytes. This is in addition to disappearance of all signs and symptoms of the disease.

Complete hematologic remission will further be classified according to suppression of the Philadelphia chromosome (Ph) as:

a) no cytogenetic response—Ph positive 100%
b) minimal cytogenetic response—Ph positive 35–95%
c) partial cytogenetic response—Ph positive 5–30%
d) complete cytogenetic response—Ph positive 0%

This will be done after a total neutrophil count of 1000/mm$^3$ has been achieved after transplant and at 6-month intervals, thereafter.

Progressive disease will be defined for purposes of the present invention as an increase in the WBC count to greater than $40 \times 10^3/\mu l$ in chronic phase, or the appearance of features of accelerated disease or blastic crisis.

Sixteen patients will be accrued as the initial human trials with the described treatment methods for leukemia. All patients treated will be valuable for both toxicity and response.

TABLE 4

Evaluation Before and During Therapy

| | Pretreatment | Every 2–3 days | When WBC count > 1.5 K/$\mu$l every 1–3 months in remission |
|---|---|---|---|
| History, physical exam | X | — | — |
| CBC, differential and platelet counts | X | X | X |
| SMA12, PT. PTT, Fib, FSP, electrolytes* | X | X | X |
| Bone marrow aspirate and biopsy | X | — | X |
| Bone marrow cytogenetics* | X | — | X |
| EKG, CXR, urinalysis* | X | — | — |
| Pulmonary function test | X | — | — |

*In addition as indicated by clinical and hematologic situations

The patient may be given subsequent processed autologous bone marrow transplants to supplement and/or further reduce the ratio of leukemic cells:normal cells in the bone marrow and peripheral blood.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 14

In vivo Treatment of Philadelphia Chromosome-Positive Leukemia Patients

The present inventors envision that either liposome/Bcr-Abl peptides (tyrosine phosphorylated or not where appropriate) or retrovirus vectors that express p160 BCR or BCR N-T fragments) will be injected i.v. periodically (daily or twice weekly) to treat their leukemia. The dose of liposome/peptides would be 100 $\mu$Moles of each peptide per 10 kg of body weight. The dose of virus would be $10^9$ infectious units per 150 kg body weight. Patients would be monitored as above for chemical response.

REFERENCES

The following references, to the extent that they provide exemplary procedural or other details supplementary to those set forth herein, are specifically incorporated herein by reference.

1. Campbell, M. L. et al. In: Advances in Cancer Research, Volume 57. Eds. G. Klein, G. F. VandeWoude, pp. 227–256. Orlando, Fla. Academic Press, Inc. 1991.
2. Arlinghaus, R. B. et al. In: UCLA Symposia on Molecular and Cellular Biology New Series. Acute Lymphoblastic Leukemia. Volume 108. Eds. R. P. Gale, D. Hoelzer, pp. 81–90. New York, N.Y. Alan R. Liss, Inc. 1990.
3. Pendergast, A. M. et al. Cell 75:175–185, 1993.
4. Liu, J. M. et al. Oncogene 8:101–109, 1993.
5. Pawson, T. et al. Cell 71:359–362, 1992.
6. McWhirter, J. R. et al. Mol. Cell Biol. 13:7587–7595, 1993.
7. Druker, B. et al. BLOOD 79:2215–2220, 1992.
8. Reichman, C. T. et al. Cell Growth & Differ., 3:451–460, 1992.
9. Ten Hoeve, J. et al. Oncogene, 8:2469–2474, 1993.
10. Sambrook, J. et al. Molecular Cloning: A Laboratory Manual, Ed. 2. Cold Spring Harbor, N.Y.: Cold Spring Harbor Laboratory, 1989.
11. Maldini, L. et al. Mol. Cell. Biol; 6:1803–1811, 1986.
12. Fioretos, M. T. et al. Oncogene, 8:2853–2855, 1993.
13. Canaani et al. In: Chronic Myelogenous Leukemia: Molecular Approaches to Research and Therapy, Deisseroth, A. and Arlinghaus, R. (Eds.), Marcel Dekker Inc., pp. 217–241, 1990.
14. Tauchi, T. et al. *J. Exp. Med.*, 179:167–175, 1994.
15. Merrifield, R., *J. Am. Chem. Soc.*, 85:2149, 1963.
16. Puil, L. et al., *EMBO Journal*, 13(4):764–773, 1994.
17. Ten Hoeve, J. et al., *Blood*, 84(6):1731–1736, 1994.
18. Campbell et al. *Oncogene*, 5:773–776, 1990.
19. Liu et al. *Oncogene*, 8:101–109, 1993.
20. Campbell and Arlinghaus. In: Advances in Cancer Research, Volume 57. eds. G. Klein, G. F. VandeWoude pp. 227–256. Orlando, Fla.: Academic Press, Inc., 1991.
21. Maru and Witte. *Cell*, 67:459–468, 1991.
22. Kyte, J., and R. F. Doolittle. J. Mol. Biol. 157:105 U.S. Pat. No. 4,554,101, 1982.
23. Adelman et al. *DNA* 2:183, 1983.
24. Messing et al. Third Cleveland Symposium on Macromolecules and Recombinant DNA. Editor: A. Walton, Elsevier Amsterdam, 1981.
25. Crea et al. PNAS 75:5765, 1978.

What is claimed is:

1. A composition comprising a Bcr-Abl peptide, wherein said peptide comprises a single tyrosine residue from position 177, a single tyrosine residue from position 283, or two tyrosine residues from positions 177 and 283 of Bcr, said composition inhibiting Bcr-Abl induction of ras.

2. The composition of claim 1, wherein said tyrosine residue is from position 177.

3. The composition of claim 2, wherein said peptide is represented by SEQ ID NO:8.

4. The composition of claim 1, wherein said tyrosine residue is from position 283.

5. The composition of claim 4, wherein said peptide is represented by SEQ ID NO:10.

6. The composition of claim 1, wherein said composition comprises two Bcr-Abl peptides, the first peptide comprising a tyrosine residue from position 177 and the second peptide comprising a tyrosine residue from position 283.

7. The composition of claim 1, further comprising a peptide or polypeptide selected from the group consisting of:
   a peptide that binds an Abl binding site on Crkl;
   a peptide that binds an Abl SH3 binding proline-rich region of Shc;
   a peptide that binds an SH2 domain of p120 ras Gap; and
   a peptide or polypeptide that binds an N-terminal coiled-coil region of Bcr.

8. The composition of claim 7, wherein the peptide or polypeptide that binds a N-terminal coiled-coil region of Bcr is further defined as having a sequence corresponding to positions 28–68 of Bcr.

9. The composition of claim 7, wherein the peptide or polypeptide is further defined as having a sequence corresponding to positions 1–71 of Bcr.

10. The composition of claim 1, wherein said peptide is further associated with a liposome.

11. The composition of claim 1, further comprising a pharmaceutically acceptable carrier.

12. A composition comprising a Bcr-Abl polypeptide, wherein said polypeptide comprises multiple tyrosine residues from position 177, multiple tyrosine residues from position 283, or multiple tyrosine residues from positions 177 and 283 of Bcr, said composition inhibiting Bcr-Abl induction of ras.

13. The composition of claim 12, wherein said polypeptide is represented by SEQ ID NO:6.

14. The composition of claim 12, wherein said polypeptide comprises tyrosine residues from positions 177 and 283 of Bcr.

15. The composition of claim 14, wherein said polypeptide comprises multiple Bcr-Abl peptides of about 10 to about 15 residues, linked by a spacer region, wherein said peptides comprise the same or a different tyrosine residue selected from positions 177 and 283 of Bcr.

16. The composition of claim 12, wherein said polypeptide is represented by SEQ ID NO:1 or SEQ ID NO:7.

17. The composition of claim 12, further comprising a peptide or polypeptide selected from the group consisting of:
   a peptide that binds an Abl binding site on Crkl;

a peptide that binds an Abl SH3 binding proline-rich region of Shc;

a peptide that binds an SH2 domain of p120 ras Gap; and a peptide or polypeptide that binds an N-terminal coiled-coil region of Bcr.

18. The composition of claim 17, wherein the peptide or polypeptide that binds a N-terminal coiled-coil region of Bcr is further defined as having a sequence corresponding to positions 28–68 of Bcr.

19. The composition of claim 17, wherein the peptide or polypeptide is further defined as having a sequence corresponding to positions 1–71 of Bcr.

20. The composition of claim 12, wherein said polypeptide is further associated with a liposome.

21. The composition of claim 12, further comprising a pharmaceutically acceptable carrier.

* * * * *

UNITED STATES PATENT AND TRADEMARK OFFICE
CERTIFICATE OF CORRECTION

PATENT NO. : 6,107,457
DATED : August 22, 2000
INVENTOR(S) : Ralph B. Arlinghaus, Jiaxin Liu, Dai Lu, and Gabriel Lopez-Berestein It is certified that error appears in the above-identified patent and that said Letters Patent is hereby corrected as shown below:

Title page, Item [56],
In reference Drucker et al., delete "Phosphorylatino" and insert
-- Phosphorylation -- therefor.
In reference Pawson and Gish, delete "Domains;" and insert -- Domains: -- therefor.
In reference Tauchi et al., delete "indpendent" and insert -- independent -- therefor.

Column 3,
Line 13, delete "AB1" and insert -- Ab1 -- therefor.
Line 23, delete "Ecr" and insert -- Bcr -- therefor.
Line 52, delete "BCR" and insert -- Bcr -- therefor.
Line 55, delete "or5-mer" and insert -- or 5-mer -- therefor.

Column 5,
Line 42, delete "bind s" and insert -- binds -- therefor.

Column 6,
Line 51, delete "various of the" and insert -- the various -- therefor.

Column 12,
Line 2, delete "Phospho serine" and insert -- Phosphoserine -- therefor.

Column 23,
Line 31, delete "Ecr" and insert -- Bcr -- therefor.

Column 34,
Line 66, delete "hyromycin" and insert -- hygromycin -- therefor.

Signed and Sealed this

Twenty-third Day of October, 2001

*Attest:*

*Attesting Officer*

NICHOLAS P. GODICI
*Acting Director of the United States Patent and Trademark Office*

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
    (A) LENGTH: 426 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:1:

```
Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
            115                 120                 125

Gly Thr Ala Arg Arg Pro Gly Ala Ala Ser Gly Glu Arg Asp Asp
    130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
        195                 200                 205

Gln Met Glu Arg Lys Lys Ser Gln His Gly Ala Gly Ser Ser Val Gly
    210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
            260                 265                 270

Pro Leu Glu Tyr Gln Pro Tyr Gln Ser Ile Tyr Val Gly Gly Met Met
        275                 280                 285

Glu Gly Glu Gly Lys Gly Pro Leu Leu Arg Ser Gln Ser Thr Ser Glu
    290                 295                 300

Gln Glu Lys Arg Leu Thr Trp Pro Arg Arg Ser Tyr Ser Pro Arg Ser
305                 310                 315                 320
```

```
            Phe Glu Asp Cys Gly Gly Gly Tyr Thr Pro Asp Cys Ser Ser Asn Glu
                            325                 330                 335

Asn Leu Thr Ser Ser Glu Glu Asp Phe Ser Ser Gly Gln Ser Ser Arg
                        340                 345                 350

Val Ser Pro Ser Pro Thr Thr Tyr Arg Met Phe Arg Asp Lys Ser Arg
                        355                 360                 365

Ser Pro Ser Gln Asn Ser Gln Gln Ser Phe Asp Ser Ser Ser Pro Pro
                        370                 375                 380

Thr Pro Gln Cys His Lys Arg His Arg His Cys Pro Val Val Val Ser
            385                 390                 395                 400

Glu Ala Thr Ile Val Gly Val Arg Lys Thr Gly Gln Ile Trp Pro Asn
                            405                 410                 415

Asp Gly Glu Gly Ala Phe His Gly Asp Ala
                            420                 425

(2) INFORMATION FOR SEQ ID NO:2:

(i) SEQUENCE CHARACTERISTICS:
            (A) LENGTH: 63 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:2:

Met Val Asp Pro Val Gly Phe Ala Glu Ala Trp Lys Ala Gln Phe Pro
        1               5                   10                  15

Asp Ser Glu Pro Pro Arg Met Glu Leu Arg Ser Val Gly Asp Ile Glu
                        20                  25                  30

Gln Glu Leu Glu Arg Cys Lys Ala Ser Ile Arg Arg Leu Glu Gln Glu
                    35                  40                  45

Val Asn Gln Glu Arg Phe Arg Met Ile Tyr Leu Gln Thr Leu Leu
                50                  55                  60

(2) INFORMATION FOR SEQ ID NO:3:

(i) SEQUENCE CHARACTERISTICS:
            (A) LENGTH: 71 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Met Val Asp Pro Val Gly Phe Ala Glu Ala Trp Lys Ala Gln Phe Pro
        1               5                   10                  15

Asp Ser Glu Pro Pro Arg Met Glu Leu Arg Ser Val Gly Asp Ile Glu
                        20                  25                  30

Gln Glu Leu Glu Arg Cys Lys Ala Ser Ile Arg Arg Leu Glu Gln Glu
                    35                  40                  45

Val Asn Gln Glu Arg Phe Arg Met Ile Tyr Leu Gln Thr Leu Leu Ala
                50                  55                  60

Lys Glu Lys Lys Ser Tyr Asp
        65                  70

(2) INFORMATION FOR SEQ ID NO:4:

(i) SEQUENCE CHARACTERISTICS:
```

(A) LENGTH: 31 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Val Gly Asp Ile Glu Gln Glu Leu Glu Arg Cys Lys Ala Ser Ile Arg
1               5                  10                  15

Arg Leu Glu Gln Glu Val Asn Gln Glu Arg Phe Arg Met Ile Tyr
            20                  25                  30

(2) INFORMATION FOR SEQ ID NO:5:

(i) SEQUENCE CHARACTERISTICS:
            (A) LENGTH: 159 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:5:

Met Val Asp Pro Val Gly Phe Ala Glu Ala Trp Lys Ala Gln Phe Pro
1               5                  10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65              70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
            115                 120                 125

Gly Thr Ala Arg Arg Pro Gly Ala Ala Ser Gly Glu Arg Asp Asp
            130                 135                 140

Arg Gly Pro Pro Ala Ser Val Ala Ala Leu Arg Ser Asn Phe Glu
145                 150                 155

(2) INFORMATION FOR SEQ ID NO:6:

(i) SEQUENCE CHARACTERISTICS:
            (A) LENGTH: 221 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:6:

Met Val Asp Pro Val Gly Phe Ala Glu Ala Trp Lys Ala Gln Phe Pro
1               5                  10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

```
Val Asn Gln Glu Arg Phe Arg Met Ile Tyr Leu Gln Thr Leu Leu Ala
     50                  55                  60

Lys Glu Lys Lys Ser Tyr Asp Arg Gln Arg Trp Gly Phe Arg Arg Ala
 65                  70                  75                  80

Ala Gln Ala Pro Asp Gly Ala Ser Glu Pro Arg Ala Ser Ala Ser Arg
                 85                  90                  95

Pro Gln Pro Ala Pro Ala Asp Gly Ala Asp Pro Pro Ala Glu Glu
                100                 105                 110

Pro Glu Ala Arg Pro Asp Gly Glu Gly Ser Pro Gly Lys Ala Arg Pro
                115                 120                 125

Gly Thr Ala Arg Arg Pro Gly Ala Ala Ser Gly Glu Arg Asp Asp
    130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
                180                 185                 190

Asp Lys Glu Val Ser Asp Arg Ile Ser Ser Leu Gly Ser Gln Ala Met
                195                 200                 205

Gln Met Glu Arg Lys Lys Ser Gln His Gly Ala Gly Ser
    210                 215                 220

(2) INFORMATION FOR SEQ ID NO:7:

(i) SEQUENCE CHARACTERISTICS:
        (A) LENGTH: 413 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Met Val Asp Pro Val Gly Phe Ala Glu Ala Trp Lys Ala Gln Phe Pro
 1               5                  10                  15

Asp Ser Glu Pro Pro Arg Met Glu Leu Arg Ser Val Gly Asp Ile Glu
                 20                  25                  30

Gln Glu Leu Glu Arg Cys Lys Ala Ser Ile Arg Arg Leu Glu Gln Glu
                 35                  40                  45

Val Asn Gln Glu Arg Phe Arg Met Ile Tyr Leu Gln Thr Leu Leu Ala
     50                  55                  60

Lys Glu Lys Lys Ser Tyr Asp Arg Gln Arg Trp Gly Phe Arg Arg Ala
 65                  70                  75                  80

Ala Gln Ala Pro Asp Gly Ala Ser Glu Pro Arg Ala Ser Ala Ser Arg
                 85                  90                  95

Pro Gln Pro Ala Pro Ala Asp Gly Ala Asp Pro Pro Ala Glu Glu
                100                 105                 110

Pro Glu Ala Arg Pro Asp Gly Glu Gly Ser Pro Gly Lys Ala Arg Pro
                115                 120                 125

Gly Thr Ala Arg Arg Pro Gly Ala Ala Ser Gly Glu Arg Asp Asp
    130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175
```

```
        Tyr Val Asn Val Glu Phe His His Glu Arg Gly Leu Val Lys Val Asn
                    180                 185                 190

Asp Lys Glu Val Ser Asp Arg Ile Ser Ser Leu Gly Ser Gln Ala Met
                195                 200                 205

Gln Met Glu Arg Lys Lys Ser Gln His Gly Ala Gly Ser Ser Val Gly
                210                 215                 220

Asp Ala Ser Arg Pro Pro Tyr Arg Gly Arg Ser Ser Glu Ser Ser Cys
        225                 230                 235                 240

Gly Val Asp Gly Asp Tyr Glu Asp Ala Glu Leu Asn Pro Arg Phe Leu
                        245                 250                 255

Lys Asp Asn Leu Ile Asp Ala Asn Gly Gly Ser Arg Pro Pro Trp Pro
                    260                 265                 270

Pro Leu Glu Tyr Gln Pro Tyr Gln Ser Ile Tyr Val Gly Gly Met Met
                    275                 280                 285

Glu Gly Glu Gly Lys Gly Pro Leu Leu Arg Ser Gln Ser Thr Ser Glu
                    290                 295                 300

Gln Glu Lys Arg Leu Thr Trp Pro Arg Arg Ser Tyr Ser Pro Arg Ser
        305                 310                 315                 320

Phe Glu Asp Cys Gly Gly Gly Tyr Thr Pro Asp Cys Ser Ser Asn Glu
                        325                 330                 335

Asn Leu Thr Ser Ser Glu Glu Asp Phe Ser Ser Gly Gln Ser Ser Arg
                    340                 345                 350

Val Ser Pro Ser Pro Thr Thr Tyr Arg Met Phe Arg Asp Lys Ser Arg
                    355                 360                 365

Ser Pro Ser Gln Asn Ser Gln Gln Ser Phe Asp Ser Ser Ser Pro Pro
            370                 375                 380

Thr Pro Gln Cys His Lys Arg His Arg His Cys Pro Val Val Val Ser
        385                 390                 395                 400

Glu Ala Thr Ile Val Gly Val Arg Lys Thr Gly Gln Ile
                        405                 410

(2) INFORMATION FOR SEQ ID NO:8:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Gly His Gly Gln Pro Gly Ala Asp Ala Glu Lys Pro Phe Tyr Val Asn
    1               5                   10                  15

Val Glu (2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Arg Ser Tyr Ser Pro Arg Ser
    1               5
```

(2) INFORMATION FOR SEQ ID NO:10:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Val Ser Pro Ser Pro Thr Thr Tyr Arg Met Phe Arg
 1               5                  10
```

(2) INFORMATION FOR SEQ ID NO:11:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Phe Leu Lys Asp Asn Leu Ile Asp Ala Asn Gly Gly Ser Arg Pro Pro
 1               5                  10                  15

Trp Pro Pro Leu Glu Tyr Gln Pro Tyr Gln Ser Ile Tyr Val Gly Gly
            20                  25                  30

Met Met Glu Gly Glu Gly Lys
            35
```

(2) INFORMATION FOR SEQ ID NO:12:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Asn Ser Leu Glu Thr Leu Leu Tyr Lys
 1               5
```

(2) INFORMATION FOR SEQ ID NO:13:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Tyr Val Asn Val
 1
```

(2) INFORMATION FOR SEQ ID NO:14:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "DNA"

(xi) SEQUENCE DESCRIPTION: SEQ ID NO:14:

CTAGTCTAGA CTAG                                                         14

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:15:

CCCCTGGAGT TCCAGCCCTA C                                                 21

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:16:

CAGAGCATCT TCGTCGGGGG C                                                 21

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:17:

CGCAGGTCCT TCTCCCCCCG G                                                 21

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:18:

GGAGGCGGCT TTACCCCGGA C                                                 21

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single

```
            (D) TOPOLOGY: linear (ii) MOLECULE TYPE: other nucleic acid
         (A) DESCRIPTION: /desc = "DNA"

(xi) SEQUENCE DESCRIPTION: SEQ ID NO:19:

TGGTCGACTC GCGACTCTTC C                                              21

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO:20:

ATCATCACCG ACACATCC                                                  18

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO:21:

GGATGTGTCG GTGATGAT                                                  18
```